(12) United States Patent
Nagano et al.

(10) Patent No.: US 9,329,184 B2
(45) Date of Patent: May 3, 2016

(54) FLUORESCENT PROBE

(75) Inventors: Tetsuo Nagano, Tokyo (JP); Kenjiro Hanaoka, Tokyo (JP); Yuichiro Koide, Tokyo (JP); Takahiro Egawa, Tokyo (JP); Yu Kushida, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 319 days.

(21) Appl. No.: 13/985,185

(22) PCT Filed: Feb. 17, 2012

(86) PCT No.: PCT/JP2012/053855
§ 371 (c)(1),
(2), (4) Date: Jul. 2, 2014

(87) PCT Pub. No.: WO2012/111818
PCT Pub. Date: Aug. 23, 2012

(65) Prior Publication Data
US 2014/0342384 A1    Nov. 20, 2014

(30) Foreign Application Priority Data
Feb. 18, 2011   (JP) .................... 2011-033396

(51) Int. Cl.
C07F 7/00 (2006.01)
C07F 7/08 (2006.01)
C12Q 1/34 (2006.01)
G01N 33/58 (2006.01)
C07F 7/10 (2006.01)
G01N 33/533 (2006.01)

(52) U.S. Cl.
CPC ............ *G01N 33/582* (2013.01); *C07F 7/0812* (2013.01); *C07F 7/0818* (2013.01); *C07F 7/10* (2013.01); *G01N 33/533* (2013.01)

(58) Field of Classification Search
CPC ........ C07F 7/10; C07F 7/0812; C07F 7/0818; G01N 33/582; G01N 33/533
USPC ........................ 556/88, 406; 436/172; 435/18
See application file for complete search history.

(56) References Cited

U.S. PATENT DOCUMENTS

2008/0014602 A1    1/2008    Nagano et al.

FOREIGN PATENT DOCUMENTS

| CN | 1810812 A | 8/2006 |
|---|---|---|
| JP | 2006-117593 A | 5/2006 |
| JP | 2008-115353 A | 5/2008 |
| WO | 99/01447 A1 | 1/1999 |
| WO | 2005/024049 A1 | 3/2005 |
| WO | 2007/100061 A1 | 9/2007 |
| WO | 2010/026743 A1 | 3/2010 |
| WO | 2010/126077 A1 | 11/2010 |
| WO | 2012/099218 A1 | 7/2012 |

OTHER PUBLICATIONS

Kushida et al., Bioorganic & Medicinal Chemistry Letters, vol. 22, pp. 3908-3911 (Published online May 2, 2012).*
GPSN Machine language translation of CN1810812A (Aug. 28, 2015).*
Koide et al., ACS Chemical Biology 6, Mar. 4, 2011, pp. 600-608.
Egawa et al., Journal of the American Chemical Society, 133, Aug. 9, 2011, pp. 14157-14159.
Egawa et al., Chemical Communications, 47, Feb. 28, 2011, pp. 4162-4164.
Best et al., Pacifichem Abstract, Dec. 19, 2010.
Koide et al., p. 8-9 (JSMI Report, p. 145), May 14, 2009.
International Search Report in International Application No. PCT/JP2012/053855, mail date is May 22, 2012.
International Preliminary Report on Patentability PCT/JP2012/053855, mail date is Aug. 29, 2013.
Japanese Office Action issued for application No. 2012-558043, mail date is May 26, 2015.

* cited by examiner

*Primary Examiner* — Porfirio Nazario Gonzalez
(74) *Attorney, Agent, or Firm* — Greenblum & Bernstein, P.L.C.

(57) ABSTRACT

A compound represented by the formula (I) ($R^1$ represents a substituent on the benzene ring; $R^2$ represents a monovalent substituent; $R^3$ and $R^4$ represent hydrogen atom, or an alkyl group; $R^5$ and $R^6$ represent an alkyl group, or an aryl group; $R^7$ and $R^8$ represent hydrogen atom, or an alkyl group; $R^9$ and $R^{10}$ represent hydrogen atom, or a monovalent substituent; and X represents silicon atom, germanium atom, or tin atom), or a salt thereof.

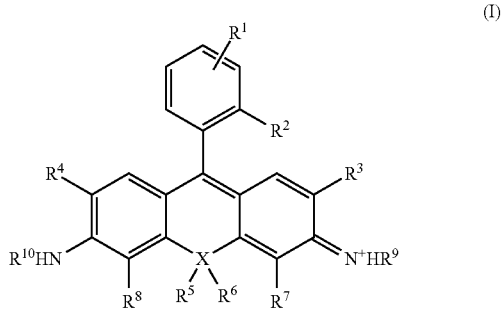

12 Claims, 5 Drawing Sheets
(5 of 5 Drawing Sheet(s) Filed in Color)

FLUORESCENT PROBE

TECHNICAL FIELD

The present invention relates to a novel fluorescent probe. More specifically, the present invention relates to a fluorescent probe that traps a measuring object substance such as proton, metal ion, reactive oxygen species, hypoxic environment, enzyme activity, glutathione and the like with a trapping group to emit fluorescence.

BACKGROUND ART

Rhodamine is a fluorescent dye known for many years similarly to fluorescein. Since both of these dyes show a high fluorescence quantum yield in water, they have been widely used in the field of biology as a fluorescent tag. Further, live cell imaging techniques utilizing a fluorescent probe have actively been used in recent years, and rhodamine is also frequently used as a parent compound for fluorescent probes that play an important role in such techniques.

As fluorescent probes having the rhodamine structure, there have so far been reported the probe for detecting nitrogen monoxide (International Patent Publication WO1999/001447), the probe for detecting hypochlorous acid (International Patent Publication WO2007/100061), and the like. Further, a compound corresponding to the basic structure of rhodamine, pyronin Y (PY), of which oxygen atom is replaced with silicon atom (TMDHS, 2,7-N,N,N',N'-tetramethyl-9-dimethyl-10-hydro-9-silaanthracene) and application of this compound as a fluorescent probe have already been reported (Best, Q et al., Pacifichem 2010, subject number 2335, Dec. 19, 2010; Yuichiro KOIDE et al., Fourth Convention of The Japanese Society for Molecular Imaging, subject number P8-9, May 14, 2009).

The fluorescent probes having TMDHS as a basic structure are basically probes utilizing the intramolecular photoinduced electron transfer (PeT) or decyclization/cyclization of Spiro ring. However, in the compounds obtained by replacing the oxygen atom of PY with silicon atom reported so far, such as TMDHS, the amino groups of the 2-position and 7-position are substituted with substituents other than hydrogen atom such as methyl group. In addition, there have not so far been reported any rhodamine analogues corresponding to rhodamine having unsubstituted amino groups at the 3-position and 6-position (such a compound may be henceforth referred to as "N,N-unsubstituted 0 rhodamine" in this specification) of which oxygen atom is replaced with silicon atom, and also there has not so far been reported any fluorescent probes utilizing such a rhodamine analogue.

PRIOR ART REFERENCES

Patent Documents

Patent document 1: International Patent Publication WO1999/001447
Patent document 2: International Patent Publication WO2007/100061 Non-patent documents
Non-patent document 1: Best, Q et al., Pacifichem 2010, subject number 2335, Dec. 19, 2010
Non-patent document 2: Yuichiro KOIDE et al., Fourth Convention of The Japanese Society for Molecular Imaging, subject number P8-9, May 14, 2009

SUMMARY OF THE INVENTION

Object to be Achieved by the Invention

An object of the present invention is to provide a novel fluorescent probe. More specifically, the object of the present invention is to provide a compound corresponding to rhodamine having unsubstituted amino groups at the 3- and 6-positions, of which oxygen atom at the 10-position of the xanthene ring moiety is replaced with silicon atom, a method for preparing such a compound, a fluorescent probe utilizing such a compound, and a method for measuring an object substance for measurement utilizing such a fluorescent probe.

Means for Achieving the Object

The inventors of the present invention conducted various researches to achieve the aforementioned object. As a result, they found that if N,N,N',N'-tetrallyldiamino-Si-xanthone was prepared by using 3-bromo-N,N-diallylaniline as a starting material, N,N,N',N'-tetrallyldiamino-Si-xanthone and a halogenated benzene derivative were reacted, and then the allyl groups were removed, a compound corresponding to rhodamine having unsubstituted amino groups at the 3- and 6-positions and having silicon atom instead of the oxygen atom at the 10-position of the xanthene ring moiety (henceforth also referred to as "N,N-unsubstituted Si rhodamine" in this specification) was successfully prepared.

Further, they also found that by introducing a group that can trap a measuring object substance (henceforth also referred to as "trapping group" in this specification) into the benzene ring at the 9-position of the N,N-unsubstituted Si rhodamine, there could be designed highly sensitive off/on type fluorescent probes or on/off type probes utilizing the intramolecular photoinduced electron transfer, and highly sensitive off/on type fluorescent probes for proton, metal ion, reactive oxygen species, hypoxic environment, enzyme activity, glutathione or the like utilizing decyclization or cyclization of spiro ring such as lactone ring and lactam ring formed by the substituent at the 2-position of the benzene ring. Furthermore, they also found that the absorption wavelength and fluorescence wavelength of the N,N-unsubstituted Si rhodamine shifted by about 90 nm to the longer wavelength side compared with rhodamine 110, which is an N,N-unsubstituted O rhodamine, and found that if one trapping group was introduced on the unsubstituted amino group at the 3- or 6-position of the xanthene ring of the N,N-unsubstituted Si rhodamine, the absorption wavelength of the N,N-unsubstituted Si rhodamine introduced with the trapping group shifted by about 90 nm to the shorter wavelength side, and therefore highly sensitive fluorescent probes for proton, metal ion, reactive oxygen species, hypoxic environment, enzyme activity, glutathione or the like utilizing such change of absorption wavelength induced by the introduction of trapping group for them were successfully designed.

For example, a compound obtained by acylating one of the unsubstituted amino groups at the 3- and 6-positions of the xanthene ring of N,N-unsubstituted Si rhodamine shows the maximum absorption wavelength around 500 nm and does not absorb lights of around 590 nm, therefore if measurement is performed with an excitation light of around 590 nm, it emits absolutely no fluorescence, but if the acyl group is removed, the maximum absorption wavelength shifts to around 590 nm, and therefore if measurement is performed with an excitation light of around 590 nm, strong fluorescence can be observed around 610 nm. By utilizing this property, a compound obtained by acylating one of the unsubstituted amino groups at the 3- and 6-positions of the xanthene ring of N,N-unsubstituted Si rhodamine can be used as a fluorescent probe for measuring peptidase, protease, or β-lactamase activity. The present invention was accomplished on the basis of the aforementioned findings.

The present invention thus provides a compound represented by the following general formula (I):

[Formula 1]

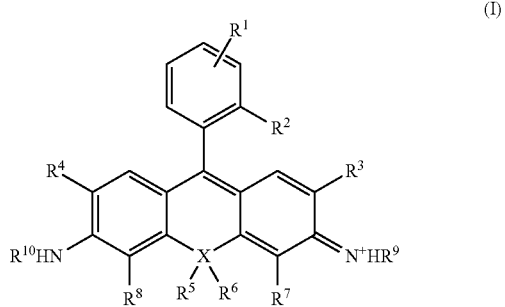

(I)

wherein, in the formula, $R^1$ represents the same or different 1 to 4 monovalent substituents existing on the benzene ring; $R^2$ represents a monovalent substituent $R^3$ and $R^4$ independently represent hydrogen atom, or an alkyl group having 1 to 6 carbon atoms; $R^5$ and $R^6$ independently represent an alkyl group having 1 to 6 carbon atoms, or an aryl group; $R^7$ and $R^8$ independently represent hydrogen atom, or an alkyl group having 1 to 6 carbon atoms; $R^9$ and $R^{10}$ independently represent hydrogen atom, or a monovalent substituent; and X represents silicon atom, germanium atom, or tin atom, or a salt thereof.

According to a preferred embodiment of the aforementioned invention, there is provided the aforementioned compound or a salt thereof, wherein $R^1$ represents hydrogen atom, or 1 or 2 monovalent substituents existing on the benzene ring (the substituent(s) is(are) selected from the group consisting of a trapping group that can trap an object substance for measurement, an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group), $R^2$ represents a monovalent substituent (the substituent is selected from the group consisting of a trapping group that can trap an object substance for measurement, an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group), $R^3$ and $R^4$ independently represent hydrogen atom, or an alkyl group having 1 to 6 carbon atoms, $R^5$ and $R^6$ independently represent an alkyl group having 1 to 6 carbon atoms, $R^7$ and $R^8$ independently represent hydrogen atom, or an alkyl group having 1 to 6 carbon atoms, $R^9$ and $R^{10}$ independently represent hydrogen atom, or a trapping group that can trap an object substance for measurement, and X represents silicon atom, or germanium atom.

According to a more preferred embodiment, there is provided the aforementioned compound or a salt thereof, wherein $R^1$ represents hydrogen atom, or 1 or 2 monovalent substituents existing on the benzene ring (the substituent(s) is(are) selected from the group consisting of a trapping group that can trap an object substance for measurement, an alkyl group having 1 to 6 carbon atoms, an alkoxy group having 1 to 6 carbon atoms, hydroxy group, carboxy group, a halogen atom, and amino group), $R^2$ represents a monovalent substituent (the substituent is selected from the group consisting of a trapping group that can trap an object substance for measurement, an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group), $R^3$ and $R^4$ represent hydrogen atom, $R^5$ and $R^6$ independently represent an alkyl group having 1 to 3 carbon atoms, $R^7$ and $R^8$ represent hydrogen atom, $R^9$ and $R^{10}$ independently represent hydrogen atom, or a trapping group that can trap an object substance for measurement, and X represents silicon atom.

In the aforementioned embodiments, $R^1$ or $R^2$, and $R^9$ and/or $R^{10}$ may be simultaneously trapping groups, but when $R^1$ or $R^2$ is a trapping group, it is preferred that $R^9$ and/or $R^{10}$ is(are) not trapping group at the same time, and when $R^9$ and/or $R^{10}$ is(are) trapping group, it is preferred that $R^1$ and $R^2$ are not trapping group at the same time. If $R^1$ or $R^2$, and $R^9$ and/or $R^{10}$ are simultaneously trapping groups, a trapping group that functions as a PeT type off/on type probe substitutes as $R^1$ or $R^2$, and a trapping group that utilizes change of absorption wavelength substitutes as $R^9$ and/or $R^{10}$, on/off of fluorescence is attained by the PeT type trapping group, the excitation wavelength is also changed by the trapping group that utilizes change of absorption wavelength, and therefore time-spatial changes of two kinds of measurement objects can be measured.

From other aspects of the present invention, there are provided the compound represented by the aforementioned general formula (I) (in the formula, $R^9$ and $R^{10}$ represent hydrogen atom) or a salt thereof for use in manufacture of a fluorescent probe, and use of the compound represented by the aforementioned general formula (I), or a salt thereof for manufacture of a fluorescent probe.

From further aspects of the present invention, there are provided a fluorescent probe for measurement of proton, a metal ion, a reactive oxygen species, a hypoxic environment, an enzyme activity, glutathione, or the like, which comprises the compound represented by the aforementioned general formula (I) (in the formula, $R^1$ or $R^2$ represents a trapping group, and $R^9$ and $R^{10}$ represent hydrogen atom) or a salt thereof; a fluorescent probe for measurement of proton, a metal ion, a reactive oxygen species, a hypoxic environment, an enzyme activity, glutathione, or the like, which comprises the compound represented by the aforementioned general formula (I) (in the formula, $R^9$ and/or $R^{10}$ represents a trapping group, and $R^1$ and $R^2$ represent a monovalent substituent other than trapping group), or a salt thereof; and a fluorescent probe for measurement of two kinds of measurement objects selected from the group consisting of proton, a metal ion, a reactive oxygen species, a hypoxic environment, an enzyme activity, and glutathione, which comprises the compound represented by the aforementioned general formula (I) (in the formula, $R^1$ or $R^2$ represents a trapping group, and $R^9$ and/or $R^{10}$ represents a trapping group), or a salt thereof. There are also provided a fluorescent probe for measurement of an enzyme activity or glutathione, which comprises the compound represented by the aforementioned general formula (I) in the formula, $R^1$ and $R^2$ represent a monovalent substituent other than trapping group, and $R^9$ and/or $R^{10}$ represents a trapping group for an enzyme activity or glutathione), or a salt thereof; and a fluorescent probe for measurement of peptidase, protease, β-lactamase, or the like, which comprises the compound represented by the aforementioned general formula (I) (in the formula, $R^1$ and $R^2$ represent a monovalent substituent other than trapping group, and $R^9$ and/or $R^{10}$ represents a trapping group for an enzyme selected from the group consisting of a peptidase, a protease, and a β-lactamase), or a salt thereof.

Further, there is also provided a method for preparing a compound represented by the aforementioned general formula (I) (in the formula, $R^3$ and $R^4$ represent hydrogen atom, $R^5$ and $R^6$ independently represent an alkyl group having 1 to 6 carbon atoms, or an aryl group; $R^7$ and $R^8$ represent hydrogen atom; $R^9$ and $R^{10}$ represent hydrogen atom; and X represents silicon atom, germanium atom, or tin atom), which comprises one or more of the following steps, preferably two or more contiguous steps among the following steps:

(a) the step of preparing a compound represented by the following general formula (II):

[Formula 2]

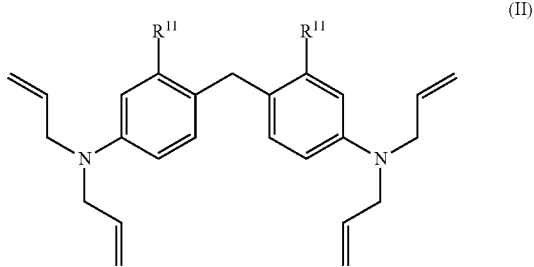

(II)

(in the formula, $R^{11}$ represents a halogen atom) from a 3-halogenated N,N-diallylaniline prepared from a 3-halogenated aniline and an allyl halide, and formaldehyde, (b) the step of reacting the compound represented by the aforementioned general formula (II) with $X(Halo)_2(R^5)(R^6)$ (Halo represents chlorine atom, or bromine atom, and X, $R^5$, and $R^6$ have the same meanings as those defined above), and then subjecting the resultant to an oxidation reaction to prepare an N,N,N',N'-tetrallyl-diamino-X-xanthone mentioned below,

[Formula 3]

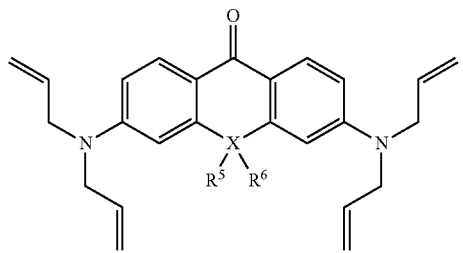

(c) the step of preparing a compound represented by the following general formula (III):

[Formula 4]

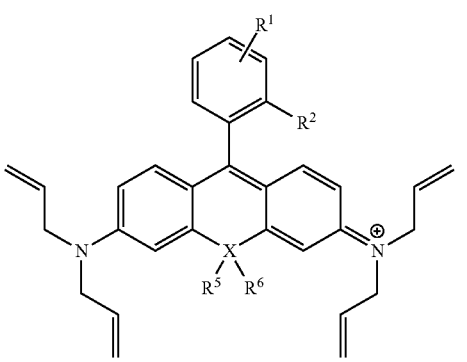

(III)

(in the formula, $R^1$ and $R^2$ have the same meanings as those defined above, but depending on types of the substituents as $R^1$ and $R^2$, protective groups are required for these substituents for the preparation of the compound of the aforementioned general formula (III), and in such a case, a protective group may be appropriately introduced into the substituents) from N,N,N',N'-tetrallyl-diamino-X-xanthone and a halogenated benzene derivative, and (d) the step of deallylating the aforementioned compound represented by the general formula (III) to prepare a compound represented by the aforementioned general formula (I) (in the formula, $R^3$ and $R^4$ represent hydrogen atom, $R^5$ and $R^6$ independently represent an alkyl group having 1 to 6 carbon atoms, or an aryl group; $R^7$ and $R^8$ represent hydrogen atom; $R^9$ and $R^{10}$ represent hydrogen atom; and X represents silicon atom, germanium atom, or tin atom) (when a protective group is introduced into $R^1$ and $R^2$ for the preparation of the compound of the aforementioned general formula (III), deprotection for the protective group may be performed before or after, or simultaneously with the step of (d)). As for the deallylation, it is also preferable to perform the deallylation after reducing the compound represented by the aforementioned general formula (III) to convert it into a 9H-xanthene compound, for improvement of the reaction yield.

Furthermore, there are also provided the aforementioned method for preparing a compound represented by the general formula (I) or a salt thereof, which comprises the aforementioned step (d); the aforementioned method for preparing a compound represented by the general formula (I) or a salt thereof, which comprises the aforementioned steps (c) and (d); the aforementioned method for preparing a compound represented by the general formula (I) or a salt thereof, which comprises the aforementioned steps (b), (c), and (d); and the aforementioned method for preparing a compound represented by the general formula (I) or a salt thereof, which comprises the aforementioned steps (a), (b), (c), and (d).

As a preferred embodiment of the aforementioned preparation method, there is also provided the method, which comprises one or more of the following steps, preferably two or more contiguous steps among the following steps:

(a) the step of preparing a compound represented by the following general formula (II):

[Formula 5]

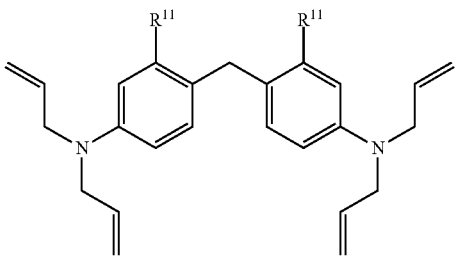

(II)

(in the formula, $R^{11}$ represents a halogen atom) from a 3-halogenated N,N-diallylaniline prepared from a 3-halogenated aniline and an allyl halide, and formaldehyde, (b) the step of reacting the compound represented by the aforementioned general formula (II) with dichlorodimethylsilane, and then subjecting the resultant to an oxidation reaction to prepare an N,N,N',N'-tetrallyl-diamino-Si-xanthone mentioned below,

[Formula 6]

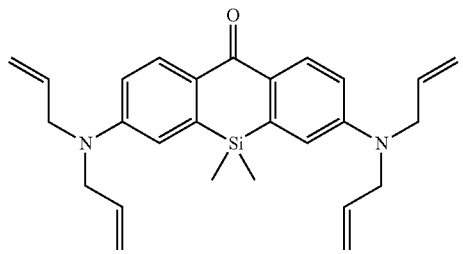

(c) the step of preparing a compound represented by the following general formula (IIIa):

[Formula 7]

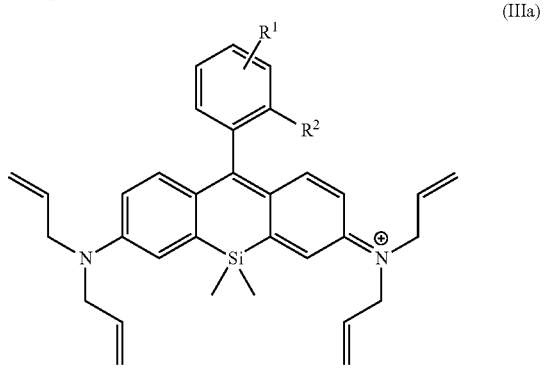

(in the formula, $R^1$ and $R^2$ have the same meanings as those defined above, but depending on types of the substituents as $R^1$ and $R^2$, protective groups are required for these substituents for the preparation of the compound of the aforementioned general formula (IIIa), and in such a case, a protective group may be appropriately introduced into the substituents) from N,N,N',N-tetrallyl-diamino-Si-xanthone and a halogenated benzene derivative, and (d) the step of deallylating the aforementioned compound of the general formula (IIIa) to prepare a compound represented by the aforementioned general formula (I) (in the formula, $R^3$ and $R^4$ represent hydrogen atom, $R^5$ and $R^6$ represent methyl group; $R^7$ and $R^8$ represent hydrogen atom; $R^9$ and $R_{10}$ represent hydrogen atom; and X represents silicon atom) (when a protective group is introduced into $R^1$ and $R^2$ for the preparation of the compound of the aforementioned general formula (IIIa), deprotection for the protective group may be performed before or after, or simultaneously with the step of (d)). As for the deallylation, it is also preferable to perform the deallylation after reducing the compound represented by the aforementioned formula (IIIa) to convert it into a 9H-xanthene compound, for improvement of the reaction yield.

Furthermore, there are also provided the aforementioned method for preparing a compound represented by the general formula (I) (in the formula, $R^3$ and $R^4$ represent hydrogen atom, $R^5$ and $R^6$ represent methyl group; $R^7$ and $R^8$ represent hydrogen atom; $R^9$ and $R^{10}$ represent hydrogen atom; and X represents silicon atom) or a salt thereof, which comprises the aforementioned step (d); the aforementioned method for preparing a compound represented by the general formula (I) (in the formula, $R^3$ and $R^4$ represent hydrogen atom, $R^5$ and $R^6$ represent methyl group; $R^7$ and $R^8$ represent hydrogen atom; $R^9$ and $R^{10}$ represent hydrogen atom; and X represents silicon atom) or a salt thereof, which comprises the aforementioned steps (c) and (d); the aforementioned method for preparing a compound represented by the general formula (I) (in the formula, $R^3$ and $R^4$ represent hydrogen atom, $R^5$ and $R^6$ represent methyl group; $R^7$ and $R^8$ represent hydrogen atom; $R^9$ and $R^{10}$ represent hydrogen atom; and X represents silicon atom) or a salt thereof, which comprises the aforementioned steps (b), (c), and (d); and the aforementioned method for preparing a compound represented by the general formula (I) (in the formula, $R^3$ and $R^4$ represent hydrogen atom, $R^5$ and $R^6$ represent methyl group; $R^7$ and $R^8$ represent hydrogen atom; $R^9$ and $R^{10}$ represent hydrogen atom; and X represents silicon atom) or a salt thereof, which comprises the aforementioned steps (a), (b), (c), and (d).

Effect of the Invention

When one or two of $R^1$, $R^2$, $R^9$, and $R^{10}$ in the compounds represented by the general formula (I) and salts thereof provided by the present invention are trapping groups for an object substance for measurement (provided that $R^1$ and $R^2$ are not simultaneously trapping groups), they have a property that fluorescence characteristics thereof observed after trapping of the object substance for measurement are different from those observed before the trapping, and by utilizing this property, the compounds represented by the general formula (I) and salts thereof can be used as compounds for preparing a fluorescent probe that enables high sensitivity measurement of an object substance for measurement such as proton, metal ion, reactive oxygen species, hypoxic environment, enzyme activity, and glutathione.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODES FOR CARRYING OUT THE INVENTION

Figure 1:
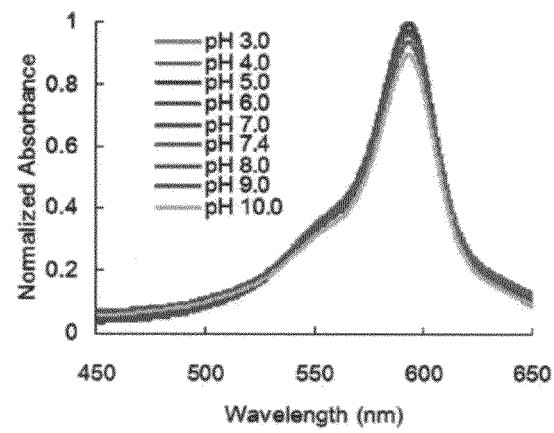
FIG. 1 shows pH profiles of absorption spectrum (upper graph) and fluorescence spectrum (lower graph) of 2-Me SiR600 (Example 2, (3)) observed in a 0.1 M sodium phosphate buffer containing 1% DMSO. Fluorescence was measured with an excitation wavelength of 593 nm.
Figure 1:
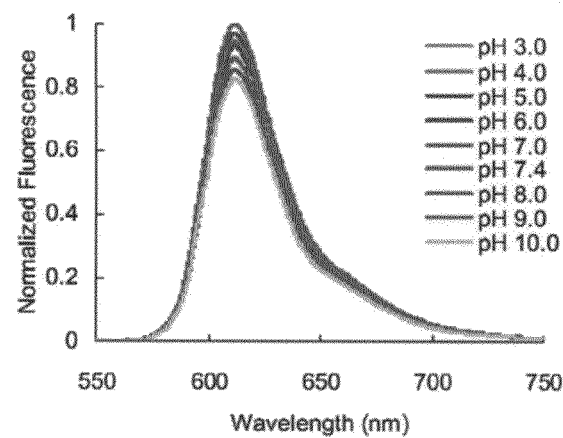

In the specification, "an alkyl group" or an alkyl moiety of a substituent containing an alkyl moiety (for example, an alkoxy group, and the like) means a linear, branched, or cyclic alkyl group, or an alkyl group consisting of a combination thereof, having, for example, 1 to 6 carbon atoms, preferably 1 to 4 carbon atoms, more preferably 1 to 3 carbon atoms, unless specifically indicated. More specifically, examples of the alkyl group include, for example, methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like. The "halogen atom" referred to in the specification may be any one of fluorine atom, chlorine atom, bromine atom, and iodine atom, preferably, fluorine atom, chlorine atom, or bromine atom.

In the compound represented by the general formula (I), $R^1$ represents hydrogen atom, or the same or different 1 to 4 monovalent substituents existing on the benzene ring. When $R^1$ represents the monovalent substituents existing on the benzene ring, it is preferred that the same or different about 1 or 2 substituents exist on the benzene ring. When $R^1$ represents one or two or more monovalent substituents, the substituents can substitute at appropriate positions on the benzene ring. It is preferred that $R^1$ represents hydrogen atom, or one substituent.

The monovalent substituent as $R^1$ may be a substituent that acts as a trapping group for an object substance for measurement. The substituent that acts as a trapping group may consist of a single substituent that acts as a trapping group, or may consist of a combination of two or more substituents on the benzene ring, preferably two adjacent substituents on the benzene ring, and act as the trapping group as such a combination. Such two substituents may bind together to form a ring structure, and such a ring structure may change into an open ring structure after a reaction with an object substance for measurement. Alternatively, two adjacent substituents may form a ring structure together with an object substance for measurement after a reaction of these two substituents with the object substance for measurement. The benzene ring may constitute a part of the trapping group for realizing the action of the trapping group. Furthermore, two or more substituents that can independently act as the trapping group may bind to the benzene ring, and two or more kinds of different substituents that act as trapping groups for different measurement object substances may exist on the benzene ring. Substitution positions of one or two or more substituents that act as the trapping group on the benzene ring are not particularly limited, and they can substitute at appropriate positions.

Type of the object substance for measurement is not particularly limited, and it may be any of, for example, proton, metal ions (for example, alkali metal ions such as sodium ion and lithium ion, alkaline earth metal ions such as calcium ion, magnesium ion, zinc ion, and the like), reactive oxygen species (for example, hydroxyl radical, peroxynitrite, hypochlorous acid, hydrogen peroxide, and the like), hypoxic environments, enzymes (peptidase, protease, lactamase, glycoside hydrolase, transferase, oxidoreductase), glutathione, and the like.

Examples of the trapping group that specifically traps an object substance for measurement include, for example:

a) as a trapping group for proton, a trapping group represented as —$CR^{20}$-A-$NR^{21}R^{22}$ (in the formula, $R^{20}$, $R^{21}$, and $R^{22}$ independently represent hydrogen atom, an alkyl group having 1 to 6 carbon atoms which may have a substituent, or an aryl group which may have a substituent, or $R^{20}$ and $R^{21}$, or $R^{20}$ and $R^{22}$ bind to represent an alkylene group having 1 to 3 carbon atoms; and A represents an alkylene group having 1 to 3 carbon atoms which may have a substituent), b) as trapping groups for a metal ion, the trapping group described in International Patent Publication WO2005/085811, page 8, [Formula 4] for sodium ion, lithium ion, potassium ion and magnesium ion (the benzene ring to which $R^3$ binds shown in International Patent Publication WO2005/085811, page 8, [Formula 4] corresponds to the benzene ring to which $R^1$ and $R^2$ bind mentioned in this specification), a trapping group having —$N(CH_2COOR^{23})_2$ (in the formula, $R^{23}$ represents hydrogen atom, a metal ion, or an ester) in a distance of 5 to 8 atoms for calcium ion (for example, —CON[$CH_2$—$CON(CH_2COOR^{23})_2]_2$, the trapping groups described in Japanese Patent Unexamined Publication (Kokai) No. 2005-201845, page 10, line 37 to page 12, line 19), and a trapping group represented as —NH—$CH_2CH_2$—$NR^{24}R^{25}$ (in the formula, $R^{24}$ and $R^{25}$ independently represent hydrogen atom, 2-pyridylmethyl group, 2-pyridylethyl group, 2-methyl-6-pyridylmethyl group, or 2-methyl-6-pyridylethyl group, but they do not simultaneously represent hydrogen atom) for zinc ion, c) as trapping group for reactive oxygen species, p-aminophenyloxymethyl group and p-hydroxyphenyloxymethyl group for peroxynitrite, hydroxyl radical and hypochlorous acid, two adjacent amino groups on a benzene ring (one of the amino groups may have one alkyl group having 1 to 6 carbon atoms) for nitrogen monoxide, and a trapping group represented as —$CH_2$—SH (this trapping group functions when it substitutes as $R^2$ in the general formula (I) disclosed in this specification, and binds to the carbon at the 10-position of the xanthene ring containing X (carbon on which the benzene ring having $R^1$ and $R^2$ substitutes) to form a thiophene ring) for hypochlorous acid, d) as a trapping group for hypoxic environments, a trapping group represented as CO—$N(R^{26})$—$B^1$—$N(R^{27})$—$B^2$—$(B^3)$r-p-$C_6H_4$—N═N—Ar—$R^{28}$ (in the formula, $R^{26}$ and $R^{27}$ independently represent hydrogen atom, or an alkyl group having 1 to 6 carbon atoms, or $R^{26}$ and $R^{27}$ may bind to each other to become an alkylene group having 2 to 6 carbon atoms; $Y^1$ represents an alkylene group having 1 to 6 carbon atoms; $B^2$ represents a single bond, —CO—, or —$SO_2$—; $B^3$ represents —O-G-$N(R^{29})$— (in the formula, G represents an alkylene group having 1 to 6 carbon atoms, and $R^{29}$ represents hydrogen atom, or an alkyl group having 1 to 6 carbon atoms); r represents 0 or 1; p-$C_6H_4$— represents p-phenylene group; Ar represents an aryldiyl group; and $R^{28}$ represents a monoalkylamino group or a dialkylamino group), e) as trapping groups for an enzyme (trapping group for an enzyme may be a monovalent substituent that is cleaved by contact with an enzyme, or a monovalent substituent to be further modified with an another substituent by contact with an enzyme), the trapping groups described in this specification, [Formula 11] to [Formula 14], those described as fluorescent probes for GGT, an acyl residue derived from an L-amino acid among 20 kinds of L-amino acids constituting proteins including an amino acid residue (amino acid residue is a group formed by removing one hydrogen atom from amino group or carboxy group of an amino acid) that substitutes on the compounds of (1) to (7) described in International Patent Publication WO2010/095450, page 12, [Formula 4] (the above amino acid residue may bind to the amino group to which $R^9$ or $R^{10}$ binds in the general formula (I) mentioned in this specification, or bind to the compounds of the general formula (I) mentioned in this specification as $R^1$ or $R^2$ via amino group, carboxy group or the like) for peptidase and protease; the trapping group described in [Formula 15] in this specification for lactamase; galactosyl group, glucosyl group, glucuronosyl group for glycoside hydrolase; hydroxy group, amino group, carboxy group, and thiol group for glucuronic acid transferase, f) as a trapping group for glutathione, the trapping group described in [Formula 16] in this specification, and the like. These trapping groups may directly substitute on the compounds represented by the general formula (I) or salts thereof, or may substitute via a spacer on the compounds represented by the general formula (I) or salts thereof.

Various trapping groups for specifically trapping an object substance for measurement have been proposed as described above, and the trapping group can be appropriately selected according to the type of the object substance for measurement. For example, there can also be used the trapping groups described in International Patent Publications WO2008/099914 and WO2008/059910 (these are for proton), Bioorg. Med. Chem. Lett., 15, pp. 1851-1855, 2005 (sodium ion and potassium ion), J. Biol. Chem., 260, pp. 3440-3450, 1985 (calcium ion), American Journal of Physiology, 256, C540-548, 1989 (magnesium ion), Japanese Patent No. 4402191, J. Am. Chem. Soc., 127, pp. 10197-10204, 2005, J. Am. Chem. Soc., 124, pp. 776-778, 2002, Cell Calcium, 31, pp. 245-251, 2002, U.S. Pat. No. 5,648,270, and Japanese Patent Unexamined Publication (Kokai) No. 2000-239272 (these are for zinc ion), International Patent Publication WO2001/064664 (reactive oxygen species), International Patent Publication WO2009/110487 (hydrogen peroxide), Japanese Patent No. 4373608, International Patent Publication WO2002/018362 (these are for singlet oxygen), Japanese Patent No. 3200024, U.S. Pat. Nos. 6,441,197, 675,623, Japanese Patent No. 3967943 (these are for nitrogen monoxide), International Patent Publication WO2010/026743, Japanese Patent Unexamined Publication (Kokai) No. 2009-275006 (these are for hypoxic environment), International Patent Publication WO2005/024049 (glycoside hydrolase), and International Patent Publication WO2010/095450 (protease), as well as those described in the catalog of Molecular Probes Inc. (Molecular Probes Handbook, 11th edition), Chapter 10 (Enzyme substrates and analysis), Chapter 17 (Signal transmission probes), Chapter 18 (Probes for reactive oxygen species including nitrogen monoxide), Chapter 19 (Indicators for calcium ion, magnesium ion, zinc ion, and other metal ions), Chapter 20 (pH Indicators), and Chapter 21 (Sodium ion, potassium ion, chloride ion, and other ions). However, the trapping group is not limited to those described in the aforementioned publications. Further, since the aforementioned publications also describe methods for using the trapping groups that specifically trap an object substance for measurement together with the trapping groups themselves, it will be readily understood by those skilled in the art that the compounds of the general formula (I) and salts thereof described in this specification can be used as a fluorescent probe for the purpose of specific measurement of an object substance for measurement.

For example, as a trapping group for nitrogen monoxide, a trapping group having the following structure can be exemplified (the benzene ring of the following trapping group corresponds to the benzene ring to which $R^1$ and $R^2$ substitute in the compounds represented by the general formula (I)). In this specification, the compound having such a structure may be referred to as diamino-N,N-unsubstituted Si rhodamine

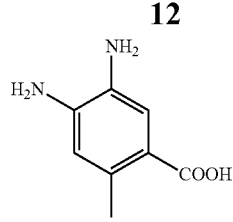

[Formula 8]

In the specification, the term "trapping" should be construed in its broadest sense which includes trapping of a metal ion or the like by chelating or the like without substantially causing chemical transformation of the trapping group, as well as trapping causing change of the chemical structure of the trapping group by chemical reaction with an object substance for measurement, and should not be construed in any limitative sense.

Concerning the compounds represented by the general formula (I) and salts thereof, the method for preparing the compounds, the fluorescent probe utilizing the compounds, and the method for measuring an object substance for measurement utilizing the fluorescent probe provided by the present invention, all the disclosures of the aforementioned publications concerning the methods and the like are incorporated into the disclosure of this specification by reference.

The monovalent substituent as $R^2$ may be a substituent that acts as a trapping group for an object substance for measurement. The substituent that acts as a trapping group may consist of a single substituent that acts as a trapping group, or may consist of a combination of $R^2$ and $R^1$ on the benzene ring and act as the trapping group as such a combination. In this case, $R^1$ at the ortho position with respect to $R^2$ and $R^2$ may bind together to form a ring structure, and such a ring structure may change into an open ring structure after the reaction with an object substance for measurement. Alternatively, $R^1$ at the ortho position with respect to $R^2$ and $R^2$ may form a ring structure together with an object substance for measurement after a reaction of these two substituents with the object substance for measurement. The benzene ring may constitute a part of the trapping group for realizing the action of the trapping group. Examples of the trapping group as $R^2$ include, for example, the aforementioned trapping groups.

When $R^2$ is a group —$(CR^{12}R^{13})_n$—Y—H [in the formula, $R^{12}$ and $R^{13}$ represent hydrogen atom, or $R^{12}$ and $R^{13}$ bind together to represent =O or =S; Y represents oxygen atom, sulfur atom, or —$NR^{14}$— (in the formula, $R^{14}$ represents a monovalent substituent) and n represents 1 or 2], $R^2$ may bind to the carbon at the 10-position of the xanthene ring containing X (carbon on which the benzene ring having $R^1$ and $R^2$ substitutes) to form a Spiro ring such as lactone ring and lactam ring. Examples of such a group include, for example, hydroxymethyl group, mercaptomethyl group, hydroxyethyl group, mercaptoethyl group, carboxy group, carboxymethyl group, carbamoyl group, —$CONHNH_2$, and the like. When the monovalent substituent as $R^2$ binds to the carbon at the 10-position of the xanthene ring containing X (carbon on which the benzene ring having $R^1$ and $R^2$ substitutes) to form a Spiro ring such as lactone ring and lactam ring, the absorption wavelength of the compound represented by the general formula (I) may be significantly shifted by cleavage of the xanthene ring conjugation system. It will be easily understood by those skilled in the art that the compounds represented by the general formula (I) may exist as such structural isomers in which a spiro ring such as lactone ring and lactam ring is formed.

The monovalent substituent as $R^{14}$ is preferably hydrogen atom, an alkyl group having 1 to 6 carbon atoms, an aryl group, or amino group, and it may be the group for trapping mercury described in Org. Lett., 12, pp. 476-479, 2010, the group for trapping diacetyl described in J. Fluoresc., 19, pp. 601-606, 2009, the group for trapping copper ion described in Org. Biomol. Chem., 8, pp. 5277-5279, 2010, or the like.

hydrolase, transferase, oxidoreductase, and the like) and glutathione. The enzyme is preferably, for example, peptidase, protease, or lactamase.

Type of the peptidase or protease is not particularly limited, so long as it is chosen so that it can hydrolyze an acyl group

[Formula 9]

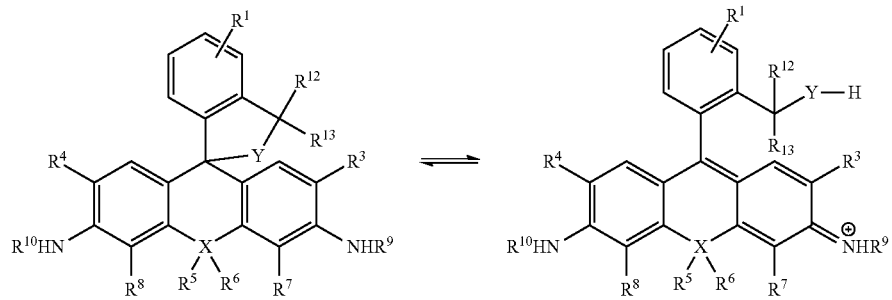

The compounds represented by the aforementioned general formula (I) may exist as a salt. Examples of the salt include base addition salts, acid addition salts, amino acid salts, and the like. Examples of the base addition salts include, for example, metal salts such as sodium salt, potassium salt, calcium salt and magnesium salt, ammonium salts, and organic amine salts such as triethylamine salt, piperidine salt, and morpholine salt, and examples of the acid addition salts include, for example, mineral acid salts such as hydrochloride, sulfate, and nitrate, and organic acid salts such as methanesulfonate, para-toluenesulfonate, citrate, and oxalate. As the amino acid salt, glycine salt, and the like can be exemplified. However, the salts of the compounds of the present invention are not limited to these examples. The same shall apply to the other compounds disclosed in this specification.

The compounds of the present invention represented by the general formula (I) may have one or two or more asymmetric carbons depending to types of substituents, and they may exist as a stereoisomer such as enantiomer and diastereoisomer. Stereoisomers in pure form, arbitrary mixtures of stereoisomers, racemates, and the like all fall within the scope of the present invention. Further, the compounds of the present invention represented by the general formula (I) and salts thereof may exist as a hydrate or a solvate, and all of these substances are encompassed by the scope of the present invention. Type of the solvent that forms the solvate is not particularly limited, and examples include, for example, such solvents as ethanol, acetone, and isopropanol. The same shall apply to the other compounds disclosed in this specification.

The fluorescent probe consisting of a compound represented by the general formula (I) (in the formula, $R^1$ and $R^2$ represent a monovalent substituent other than a trapping group, and $R^9$ and/or $R^{10}$ represents a trapping group) provided by the present invention can generate a compound showing an absorption wavelength shifted to the longer wavelength side (corresponding to a compound of the aforementioned general formula (I) wherein $R^9$ and/or $R^{10}$ is unsubstituted amino group) after the trapping group(s) as $R^9$ and/or $R^{10}$ is(are) cleaved by contact with an object substance for measurement, and thus it can be preferably used as a fluorescent probe for measurement of the object substance for measurement. Examples of the object substance for measurement include enzymes (peptidase, protease, lactamase, glycoside in the compounds of the present invention represented by the aforementioned general formula (I) wherein $R^9$ and/or $R^{10}$ is the acyl group. The peptidase may be an endopeptidase or an exopeptidase, and the protease may be an endoprotease or an exoprotease. For example, in order to measure a peptidase or protease of which substrate is a specific amino acid, an acyl residue derived from that amino acid can be used as $R^9$ and/or $R^{10}$, and by using a compound designed in this way, a particular peptidase or protease can be specifically measured (the acyl residue derived from the amino acid correspond to a partial structure of the amino acid remaining after removal of hydroxy group from the carboxy group of the amino acid). From this point of view, in the fluorescent probe for a peptidase or protease, it is preferable to use an acyl residue derived from an amino acid that can be hydrolyzed with the peptidase or protease as $R^9$ and/or $R^{10}$. For example, there can be used acyl residues derived from 20 kinds of the L-amino acids that constitutes proteins, as well as acyl residues derived from selenocysteine, pyrrolysine, cystine, hydroxyproline, hydroxylysine, tyroxine, O-phosphoserine, desmosine, β-alanine, sarcosine, ornithine, creatine, γ-aminobutyric acid, opine, and the like.

Structural change of the compounds having the trapping group as $R^{10}$ and giving shift of absorption wavelength to the longer wavelength side induced by cleavage of $R^{10}$ by contact with an object substance for measurement (the compounds after the structural changes correspond to the compounds of the aforementioned general formula (I) wherein $R^9$ and/or $R^{10}$ is(are) unsubstituted amino group) is shown below. In the following formulas, $R^1$ and $R^2$ are collectively shown by R for convenience.

[Formula 10]

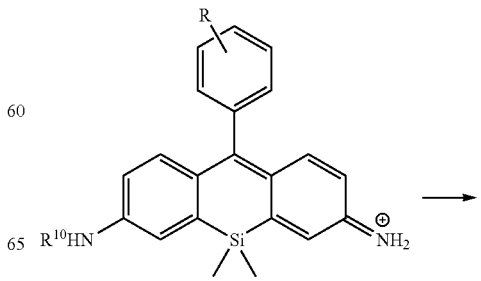

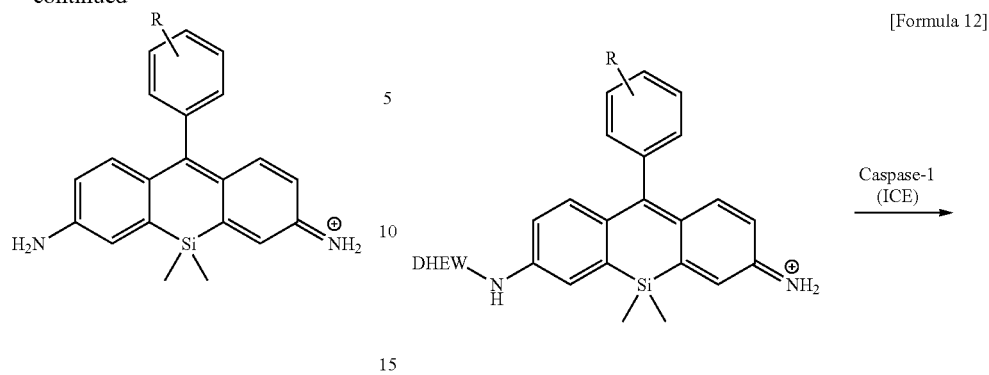

preferred example of $R^{10}$ for the case where the protease is caspase 3 is shown below. DEVD is an indication based on the one-letter codes of amino acids. In this specification, this compound may be referred to as N-DEVD-substituted Si rhodamine.

[Formula 11]

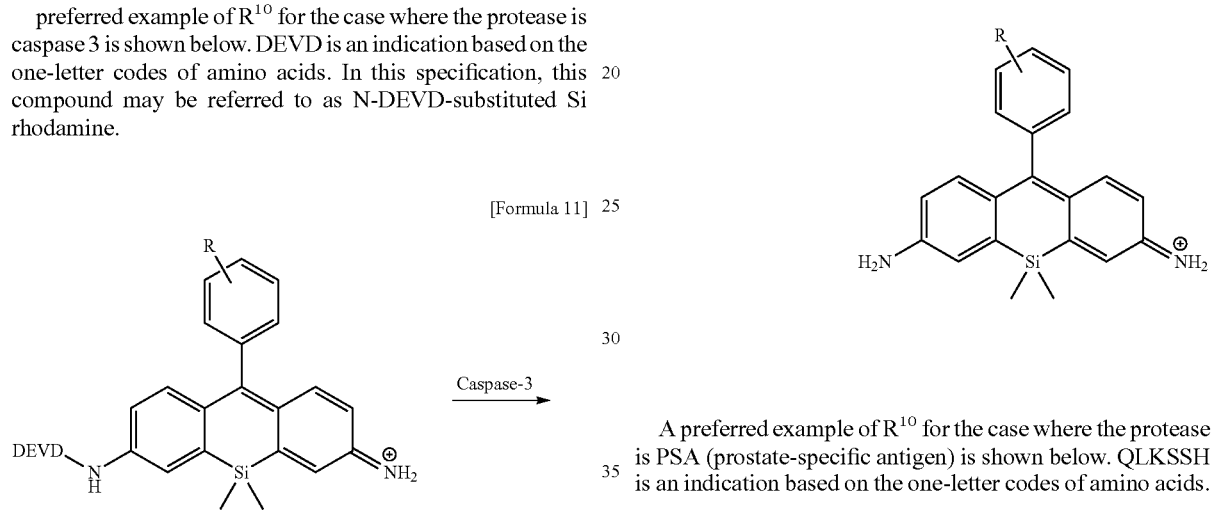

A preferred example of $R^{10}$ for the case where the protease is caspase 1 (also referred to as ICE) is shown below. DHEW is an indication based on the one-letter codes of amino acids.

[Formula 12]

A preferred example of $R^{10}$ for the case where the protease is PSA (prostate-specific antigen) is shown below. QLKSSH is an indication based on the one-letter codes of amino acids.

[Formula 13]

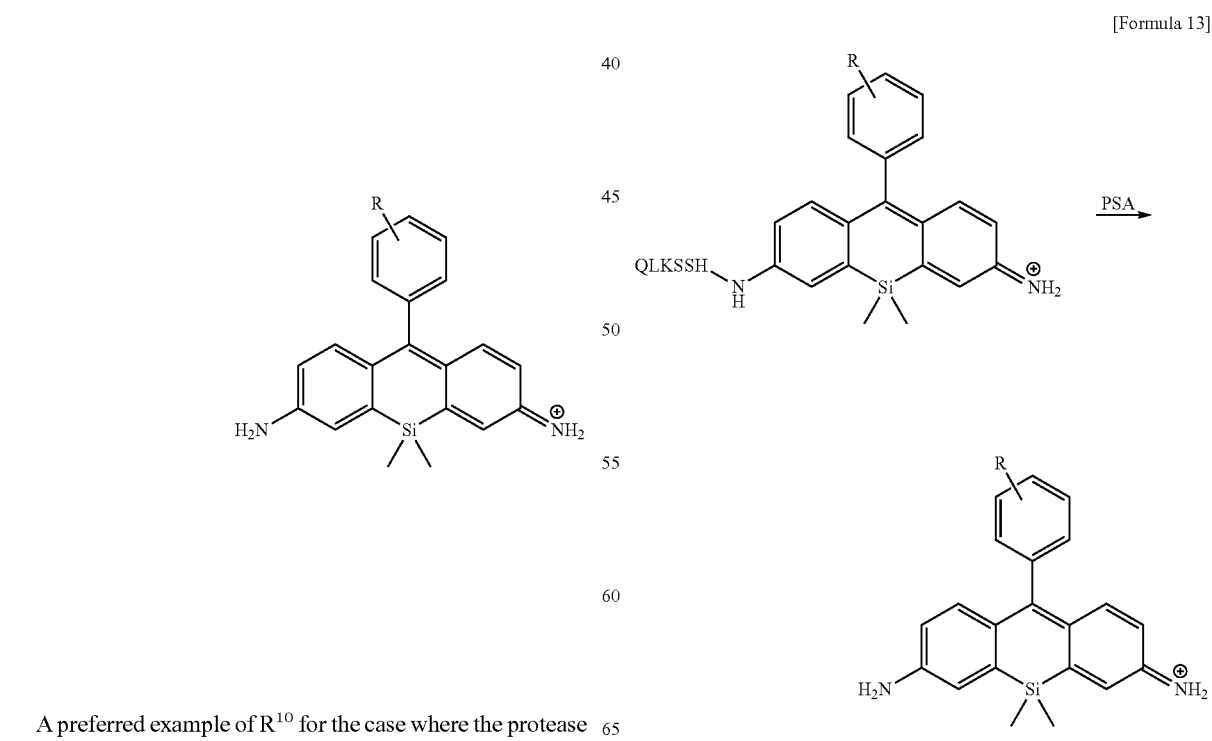

A preferred example of $R^{10}$ for the case where the peptidase is LAP (leucine aminopeptidase) is shown below.

[Formula 14]

example, if the following compound is used instead of $_\gamma$gluRhoHM in accordance with the method described in WO2011/087000, cancer cells and cancer tissues can be specifically measured, and therefore it can be used as a cancer diagnostic agent.

[Formula 15]

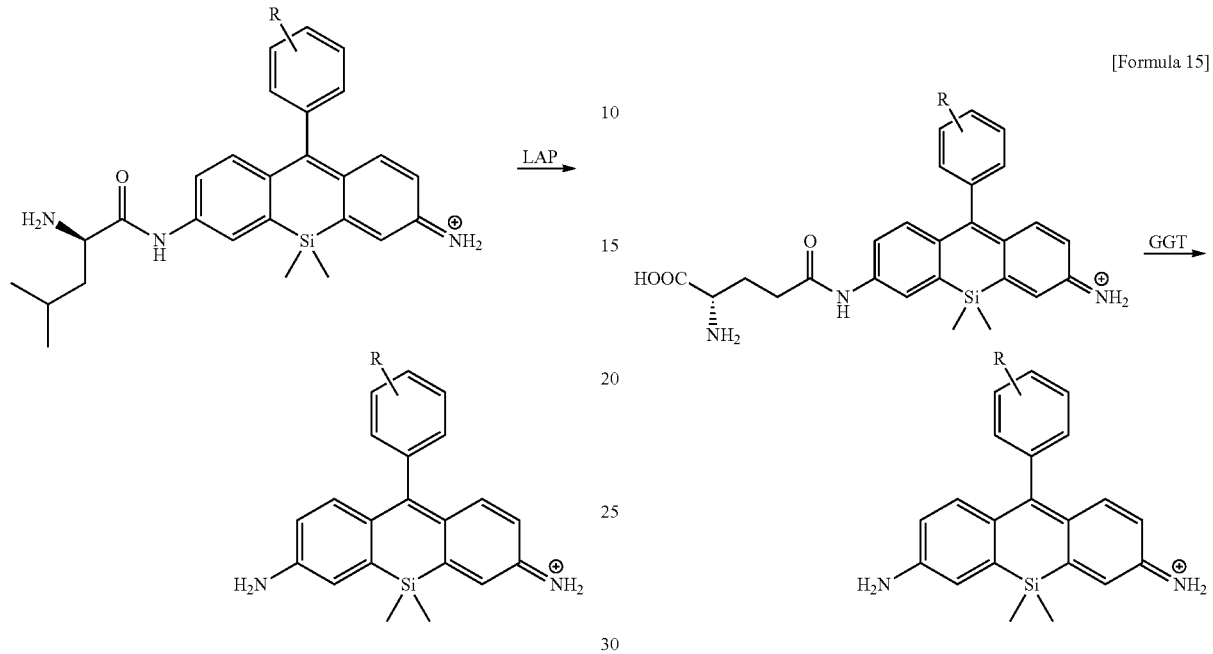

A preferred example of $R^{10}$ for the case where the peptidase is GGT ($_\gamma$-glutamyl transpeptidase) is shown below. For A preferred example of $R^{10}$ for the case where the lactamase is β-lactamase is shown below.

[Formula 16]

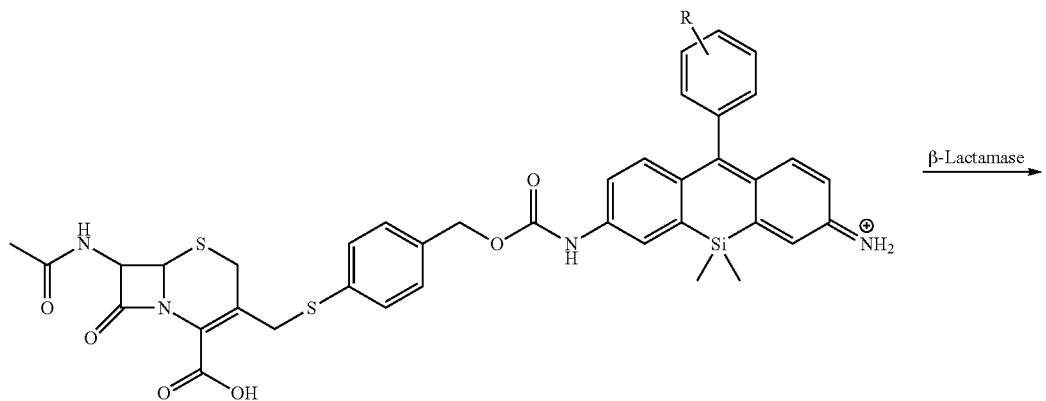

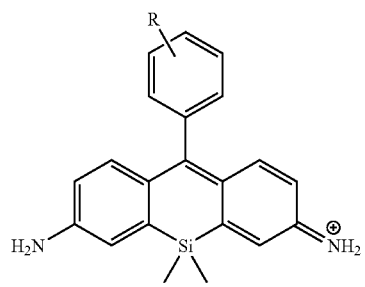

A preferred example of $R^{10}$ for the case where the object substance for measurement to be cleaved by the contact is glutathione is shown below.

[Formula 17]

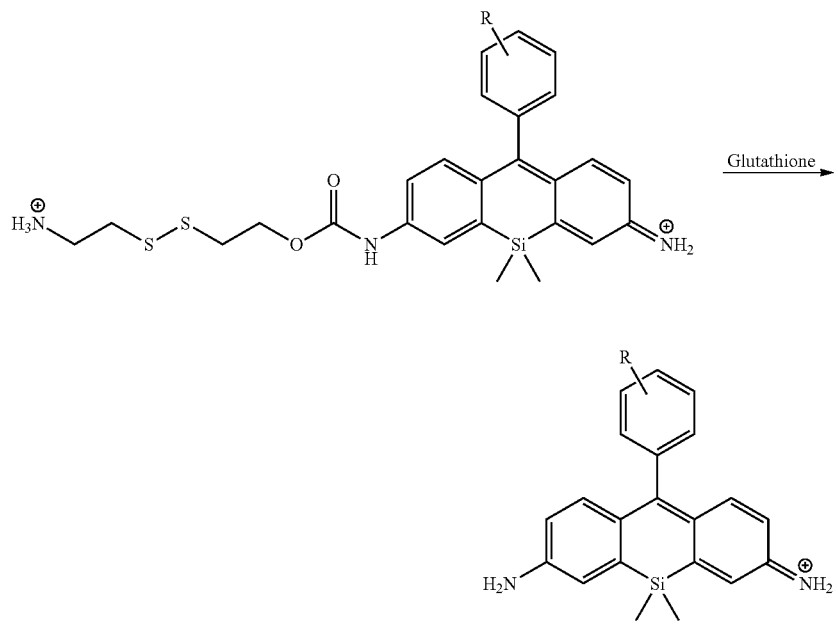

Since measurement of an object substance for measurement can be performed by using the aforementioned various fluorescent probes according to the methods well known to those skilled in the art such as the methods disclosed in the publications mentioned above for the trapping groups, besides as reagents for researches, they can also be used as reagents for diagnoses of animals and humans. For example, use of the aforementioned various fluorescent probes makes it possible to measure concentration or quantity of an object substance for measurement in vitro, or an object substance for measurement can be measured in vivo by incorporating them into live cells or living bodies, and imaging them with bioimaging techniques. Typical examples include a method for measuring an object substance for measurement, which comprises the following steps: (a) the step of contacting a compound represented by the general formula (I) or a salt thereof and the object substance for measurement, and (b) the step of measuring fluorescence intensity of a compound generated in the step (a) after trapping of the object substance for measurement.

As described above, in the compounds of the present invention, appropriate substituents can be easily incorporated as $R^9$ and/or $R^{10}$ by a well-known method. For example, it will also be easily understood by those skilled in the art that functional substituents other than the trapping group, such as a substituent for labeling and a substituent for forming caged compounds, can be introduced. In addition, the term "measurement" used in this specification must be construed in its broadest sense including quantification, qualification, as well as measurement, examination, detection, and the like performed for the purposes of diagnosis and the like.

The compounds of the present invention can be synthesized according to the following synthesis scheme.

[Formula 18]

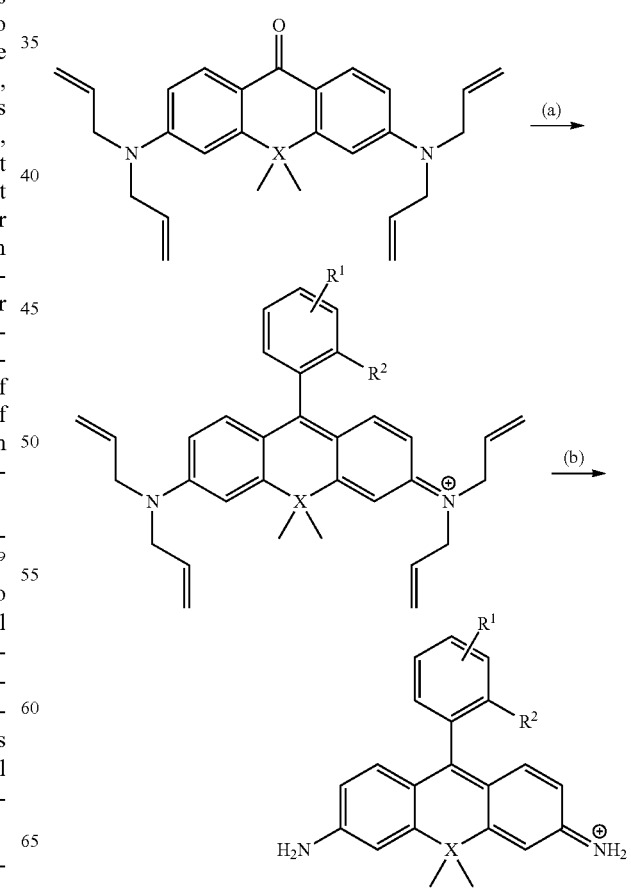

(1) Step (a)

Since International Patent Publication WO2005/085811 discloses a method for synthesizing N,N,N',N'-tetramethylrhodamine derivative by using an analogous compound of N,N,N,N'-tetrallyl-diamino-Si-xanthone synthesized in Example 1, which has oxygen atom instead of the silicon atom (3,6-bisdimethylaminoxanthone), N,N,N',N'-tetrallyl-diamino-Si-rhodamine derivatives can be synthesized from N,N,N',N'-tetrallyl-diamino-Si-xanthone by referring to the above synthesis method. For example, an N,N,N',N'-tetrallyl-diamino-Si-rhodamine derivative can be synthesized by adding sec-butyllithium to a halogenated benzene derivative in an amount of 1 to 1.1 equivalents with respect to the halogenated benzene derivative at −78° C. in a solvent, then adding N,N,N',N'-tetrallyl-diamino-Si-xanthone in an amount of ⅕ equivalent with respect to the halogenated benzene derivative, and performing a treatment with hydrochloric acid. Further, since specific examples of the methods for preparing N,N,N',N'-tetrallyl-diamino-X-rhodamine containing silicon atom or germanium atom as X are disclosed in the examples of this specification, N,N,N',N'-tetrallyl-diamino-X-rhodamine derivatives can be synthesized by referring to them.

(2) Step (b)

The allyl protective group for N,N,N',N'-tetrallyl-diamino-Si-xanthone is one of the protective groups of amino group frequently used in the organic synthesis, and can easily be removed by a treatment with a catalytic amount of tetrakis(triphenylphosphine)palladium and 5 to 6 equivalents of 1,3-dimethylbarbituric acid. As for the deallylation, it is also preferable to perform the deallylation after reducing the aforementioned compound of the general formula (III) to convert it into a 9H-xanthene compound, for improvement of the reaction yield.

By appropriately combining the synthesis methods of Examples 1 and 2 mentioned above and known methods, the fluorescent probes having a trapping group as $R^1$ or $R^{10}$ can be obtained.

Although the method for using the fluorescent probe of the present invention is not particularly limited, for example, nitrogen monoxide can be measured according to the method disclosed in International Patent Publication WO1999/001447 as a method for measuring nitrogen monoxide. For example, nitrogen monoxide generated in a reaction mixture by using NOC-12 and NOC-13, which are spontaneous nitrogen monoxide generators, can be contacted and reacted with diamino-N,N-unsubstituted X rhodamine. The NOC at various concentrations can be added to a diamino-N,N-unsubstituted X rhodamine solution by using, for example, a 0.1 M phosphate buffer (pH 7.4) as the reaction solvent to allow the reaction at 37° C., and then fluorescence intensity can be measured with a spectrofluorometer by using appropriate excitation wavelength and fluorescence wavelength to measure generation amount of nitrogen monoxide.

Further, the enzymatic activity of caspase 3 can be measured according to the method disclosed in the Japanese Patent Unexamined Publication (Kohyo) No. 2004-521080 as a caspase activity measurement method based on cleavage of a fluorescent substrate. As a standard reaction mixture (final volume, 300 μL), a mixture containing N-DEVD-substituted Si rhodamine and purified or crude caspase 3 enzyme in 50 mM HEPES/KOH (pH 7.0), 10% (volume basis) glycerol, 0.1% (w/v) CHAPS, 2 mM EDTA, 5 mM dithiothreitol can be incubated at 25° C., and the reaction can be continuously monitored with a spectrofluorophotometer by using appropriate excitation wavelength and fluorescence wavelength to measure the enzymatic activity of caspase

3. The Specific Procedures are Disclosed in the Examples of this Specification

EXAMPLES

Hereafter, the present invention will be more specifically explained with reference to examples. However, the scope of the present invention is not limited by the following examples. In the examples, Me means methyl group, and Ac means acetyl group.

Example 1

In accordance with the following scheme, there was synthesized N,N,N',N'-tetrallyl-diamino-Si-xanthone, which is a synthetic intermediate of the compounds of the present invention represented by the general formula (I) (in the formula, $R^3$ and $R^4$ represent hydrogen atom; $R^5$ and $R^6$ represent methyl group; $R^7$ and $R^8$ represent hydrogen atom; $R^9$ and $R^{10}$ represent hydrogen atom; and X represents silicon atom). In a similar manner, the compound wherein X is germanium atom, and the compound wherein $R^5$ and $R^6$ are ethyl groups were also synthesized.

[Formula 19]

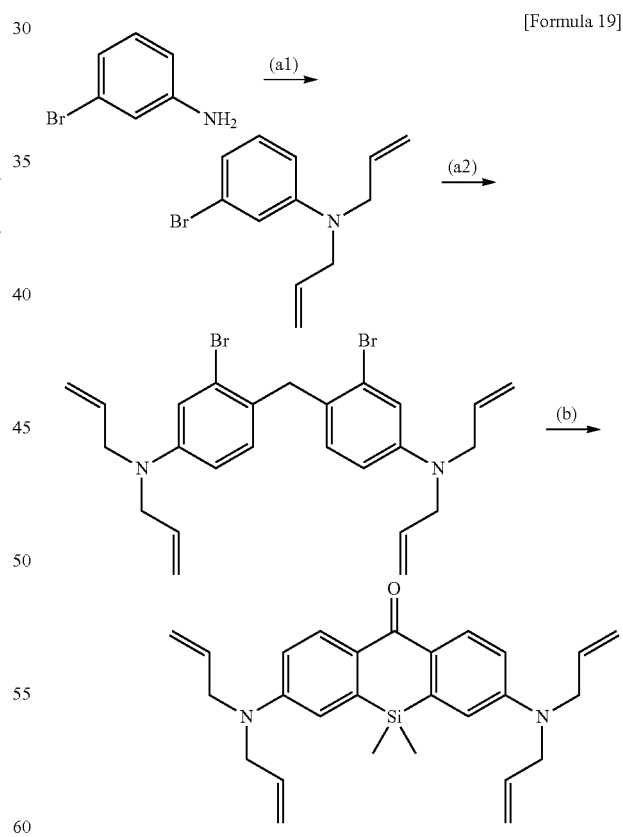

(1) Step (a1)

Potassium carbonate (22.0 g, 159 mmol) was suspended in acetonitrile, 3-bromoaniline (8.71 mL, 80.0 mmol) and allyl bromide (23.7 mL, 280 mmol) were added to the suspension, and the mixture was stirred at 80° C. for 14 hours. The reaction mixture was cooled to room temperature, then filtered through Celite, and sufficiently washed with ethyl acetate. The solvent was removed, and then the residue was purified by column chromatography (silica gel, ethyl acetate/hexane (1/40)) to obtain 3-bromo-N,N-diallylaniline (17.1 g, 67.9 mmol, yield 85%).

$^1$H-NMR (300.40 MHz, CDCl$_3$): δ 3.87-3.90 (m, 4H), 5.11-5.15 (m, 2H), 5.17-5.18 (m, 2H), 5.75-5.88 (m, 2H), 6.58 (dd, 1H, J=2.2, 8.1 Hz), 6.77-6.81 (m, 2H), 7.01 (t, 1H, J=8.1 Hz)

$^{18}$C-NMR (75.45 MHz, CDCl$_3$): δ 52.7, 110.8, 115.0, 116.3, 119.0, 123.3, 130.2, 133.2, 150.0

HRMS (ESI+): Found 252.0429, calculated 252.0388 for [M+H]+ (+4.1 mmu)

(2) Step (a2)

3-Bromo-N,N-diallylaniline (17.1 g, 67.9 mmol) was dissolved in acetic acid (200 mL), 37% formaldehyde solution (10.2 g, 340 mmol) was added to the solution, and the mixture was heated at 80° C. for 75 minutes. The reaction mixture was cooled to room temperature, and then neutralized with saturated aqueous sodium hydrogencarbonate and sodium hydroxide. This mixture was extracted with dichloromethane, and the organic layer was washed with brine. The organic layer was dried over sodium sulfate, the solvent was removed, and then the residue was purified by column chromatography (silica gel, ethyl acetate/hexane (1/30)) to obtain bis(2-bromo-4-N,N-diallylaminophenyl)methane (15.2 g, 29.5 mmol, yield 87%).

$^1$H-NMR (300.40 MHz, CDCl$_3$): δ 3.85-3.87 (m, 8H), 3.96 (s, 2H), 5.13-5.19 (m, 8H), 5.76-5.88 (m, 4H), 6.54 (dd, 2H, J=2.9, 8.8 Hz), 6.81 (d, 2H, J=8.1 Hz), 6.90 (d, 2H, J=2.9 Hz)

$^{13}$C-NMR (75.45 MHz, CDCl$_3$): δ 39.7, 52.7, 111.7, 116.0, 116.2, 125.5, 126.9, 130.8, 133.5, 148.1

HRMS (ESI+): Found 517.0654, calculated 517.0677 for [M+14]+ (−2.3 mmu)

(3) Step (b)

Bis(2-bromo-4-N,N-diallylaminophenyl)methane (8.16 g, 15.8 mmol) and anhydrous tetrahydrofuran (THF, 50 mL) were added to a dried flask under an argon atmosphere. The mixture was cooled to −78° C., and then 1 M sec-butyllithium (45 mL, 45 mmol) was added, and the mixture was stirred for 20 minutes. dichlorodimethylsilane (2.9 mL, 30 mmol) dissolved in anhydrous THF (10 mL) was slowly added to the mixture at the same temperature, and the mixture was brought to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (150 mL), the solution was cooled to 0° C. and potassium permanganate (6.88 g, 43.5 mmol) was added portionwise into the solution over 2 hours, and the mixture was further stirred at the same temperature for 1 hour. Dichloromethane (200 mL) was added to the mixture, and the mixture was subjected to suction filtration using filter paper. The solvent was removed, and the residue was purified by column chromatography (silica gel, dichloromethane) to obtain N,N,N',N'-tetraallyl-diamino-Si-xanthone (2.23 g, 5.20 mmol, yield 33%).

$^1$H-NMR (300.40 MHz, CDCl$_3$): δ 0.41 (s, 6H), 4.02 (d, 8H, J=5.1 Hz), 5.17-5.23 (m, 8H), 5.82-5.94 (m, 4H), 6.80-6.83 (m, 4H), 8.34 (d, 2H, J=8.1 Hz)

$^{13}$C-NMR (75.45 MHz, CDCl$_3$): δ −1.1, 52.8, 113.5, 114.8, 116.7, 130.0, 131.7, 133.1, 140.5, 150.2, 185.1

HRMS (ESI+): Found 429.2347, calculated 429.2362 for [M+H]+ (−1.5 mmu)

(4) N,N,N',N'-3,6-Tetraallyldiamino-Ge-xanthone

Bis(2-bromo-4-N,N-diallylaminophenyl)methane (6.16 g, 11.9 mmol) and anhydrous THF (40 mL) were added to a dried flask under an argon atmosphere. The mixture was cooled to −78° C., and then 1 M sec-butyllithium (BuLi, 34 mL, 34 mmol) was added, and the mixture was stirred for 20 minutes. Dichlorodimethylgermane (2.62 mL, 22.7 mmol) dissolved in anhydrous THF (15 mL) was slowly added to the mixture at the same temperature, and the mixture was brought to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (120 mL), and the solution was cooled to 0° C. Potassium permanganate (5.20 g, 32.9 mmol) was added portionwise to the solution over 2 hours, and the mixture was further stirred at the same temperature for 1 hour. The mixture was added with dichloromethane (200 mL), and the mixture was subjected to suction filtration using filter paper. Then, the solvent was removed, and the residue was purified by column chromatography (silica gel, dichloromethane) to obtain the objective substance (1.29 g, 2.72 mmol, yield 23%).

$^1$H NMR (300 MHz, CDCl$_3$): δ 0.54 (s, 6H), 4.00-4.02 (m, 8H) 5.17-5.23 (m, 8H), 5.81-5.94 (m, 4H), 6.72 (d, 2H, J=2.9 Hz), 6.78 (dd, 2H, J=2.6, 9.2 Hz), 8.36 (d, 2H, J=8.8 Hz)

$^{13}$C NMR (75 MHz, CDCl$_3$): δ −1.8, 52.3, 112.6, 114.4, 116.2, 129.6, 131.7, 132.7, 142.8, 149.8, 184.5

LRMS (ESI+): m/z Found 475, calculated 475 for [M+H]+

(5) 3,6-Diamino-Ge-xanthone

Tetrakis(triphenylphosphine)palladium (330 mg, 0.285 mmol) and 1,3-dimethylbarbituric acid (1.41 g, 9.04 mmol) were added to a dried flask under an argon atmosphere. N,N,N',N'-Tetraallyldiamino-Ge-xanthone (1.00 g, 2.11 mmol) dissolved in dichloromethane (50 mL) was added to the mixture, and the mixture was stirred at 35° C. for 16 hours. The solvent was removed, the residue was suspended in saturated aqueous sodium hydrogencarbonate, and the suspension was extracted with dichloromethane. The organic layer was dried over sodium sulfate, the solvent was removed, and then the residue was purified by column chromatography (silica gel, ethyl acetate/hexane (4/3)) to obtain a 3,6-diamino-Ge-xanthone mixture (760 mg, quantitative).

$^1$H NMR (300 MHz, CD$_3$OD): δ 0.55 (s, 6H), 6.73-6.76 (m, 4H), 8.33 (d, 2H, J=9.5 Hz)

$^{13}$C NMR (75 MHz, CD$_3$OD): δ −1.9, 116.1, 118.3, 130.9, 133.2, 145.2, 152.9, 187.3

LRMS (ESI+): m/z Found 315, calculated 315 for [M+H]+

(6) N,N,N',N'-3,6-Tetraallyldiamino-diethyl-Si-xanthone

Bis(2-bromo-4-N,N-diallylaminophenyl)methane (1.65 g, 3.20 mmol) and anhydrous THF (20 mL) were added to a dried flask under an argon atmosphere. The mixture was cooled to −78° C., and then 1 M sec-BuLi (10 mL, 10 mmol) was added, and the mixture was stirred for 20 minutes. Dichlorodiethylsilane (1.04 mL, 7.02 mmol) dissolved in anhydrous THF (5 mL) was slowly added to the mixture at the same temperature, and the mixture was brought to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (50 mL), and the solution was cooled to 0° C. Potassium permanganate (1.49 g, 9.43 mmol) was added portionwise to the solution over 2 hours, and the mixture was further stirred at the same temperature for 1 hour. Dichloromethane (50 mL) was added to the mixture, and the mixture was filtered through Celite. Then, the solvent was removed, and the residue was purified by column chromatography (silica gel, hexane/ethyl acetate (10/1)) to obtain N,N,N',N'-3,6-tetraallyldiamino-diethyl-Si-xanthone (419 g, 0.917 mmol, yield 29%).

$^1$H NMR (300 MHz, CDCl$_3$): δ 0.91 (s, 10H), 4.01-4.02 (m, 8H), 5.17-5.22 (m, 8H), 5.82-5.94 (m, 4H), 6.79-6.84 (m, 4H), 8.35 (d, 2H, J=8.8 Hz)

$^{13}$C NMR (75 MHz, CDCl$_3$): δ 5.56, 7.48, 52.7, 113.3, 115.0, 116.5, 130.9, 131.6, 133.1, 138.3, 149.9, 185.3

HRMS (ESI+): m/z Found 457.2661, calculated 457.2675 for [M+H]+ (−1.5 mmu)

(7) 3,6-Diamino-diethyl-Si-xanthone

Tetrakis(triphenylphosphine)palladium (204 mg, 0.176 mmol) and 1,3-dimethylbarbituric acid (1.04 g, 6.67 mmol) were added to a dried flask under an argon atmosphere. N,N,N',N'-Tetraallyldiamino-diethyl-Si-xanthone (419 mg, 0.917 mmol) dissolved in dichloromethane (30 mL) was added to the mixture, and the mixture was stirred at 35° C. for 16 hours. The solvent was removed, the residue was suspended in saturated aqueous sodium hydrogencarbonate, and the suspension was extracted with dichloromethane. The organic layer was dried over sodium sulfate, the solvent was removed, and then the residue was purified by column chromatography (silica gel, ethyl acetate/hexane (4/5)) to obtain 3,6-diamino-diethyl-Si-xanthone (236 mg, 0.796 mmol, yield 87%).

$^1$H NMR (300 MHz, CDCl$_3$): δ 0.83-0.95 (m, 10H), 4.10 (s, 4H), 6.76-6.81 (m, 4H), 8.33 (d, 2H, J=7.8 Hz)

$^{13}$C NMR (75 MHz, CDCl$_3$): δ 5.37, 7.38, 116.2, 117.5, 132.0, 132.9, 138.8, 148.9, 185.5

HRMS (ESI+): m/z Found 297.1462, calculated 297.1423 for [M+H]+ (3.9 mmu)

Example 2

By using N,N,N',N'-tetrallyl-diamino-Si-xanthone synthesized in Example 1, there was synthesized a compound of the present invention represented by the general formula (I) or a salt thereof, wherein R$^1$ was hydrogen atom, R$^2$ was methyl group or carboxyl group, R$^3$ and R$^4$ were hydrogen atoms, R$^5$ and R$^6$ were methyl groups, R$^7$ and R$^8$ were hydrogen atoms, R$^9$ and R$^{10}$ were hydrogen atoms, and X was silicon atom.

Further, a compound corresponding to the aforementioned compound in which acetyl group was introduced as R$^{10}$ was also synthesized.

(1) N,N,N',N'-tetrallyl-2-methyl SiR600

[Formula 20]

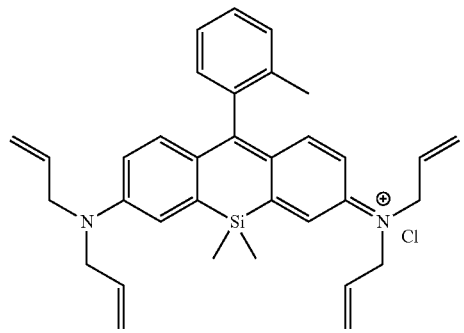

2-Bromotoluene (253 μL, 2.10 mmol) and anhydrous THF (25 mL) were added to a sufficiently dried flask under an argon atmosphere. The mixture was cooled to −78° C., and then 1 M sec-butyllithium (2.3 mL, 2.3 mmol) was added, and the mixture was stirred for 20 minutes. N,N,N',N'-Tetrallyl-Si-xanthone (180 mg, 0.42 mmol) dissolved in anhydrous THF (5 mL) was slowly added to the mixture at the same temperature, and the mixture was brought to room temperature. The mixture was stirred at room temperature for 30 minutes, and then 2 N hydrochloric acid (6 mL) was added, and the mixture was stirred for 10 minutes. This mixture was extracted with dichloromethane, and the organic layer was washed with brine. The organic layer was dried over sodium sulfate, the solvent was evaporated under reduced pressure, and then the residue was purified by column chromatography (silica gel, 5% methanol/dichloromethane) to obtain N,N,N',N'-tetrallyl-2-methyl SiR600 (215 mg, 0.40 mmol, yield 95%).

$^1$H-NMR (300 MHz, CD$_3$OD): δ 0.55 (s, 3H), 0.57 (s, 3H), 2.04 (s, 3H), 4.31 (d, J=5.1 Hz, 8H), 5.19-5.31 (m, 8H), 5.88-6.00 (m, 4H), 6.79 (dd, J=9.6 Hz, 3.0 Hz, 2H), 7.10-7.13 (m, 3H), 7.33-7.47 (m, 5H)

$^{13}$C-NMR (100 MHz, CDCl$_3$): δ −1.57, −1.32, 19.51, 54.64, 115.87, 118.13, 122.89, 126.79, 129.13, 130.12, 131.35, 132.58, 136.89, 139.85, 142.91, 149.83, 155.52, 172.10

HRMS (ESI+): Calcd for [M]+ 503.2882. Found 503.2856 (−2.7 mmu)

(2) 9-o-Toluyl-9H—Si-xanthene-3,6-diamine

[Formula 21]

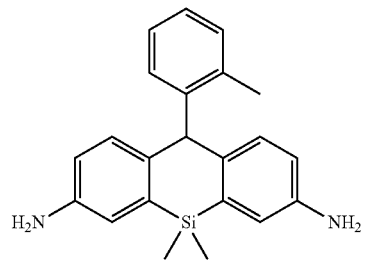

N,N,N',N'-Tetraallyl-2-methyl SiR600 (350 mg, 0.65 mmol) was dissolved in methanol (20 mL), and sodium borohydride (29 mg, 0.77 mmol) was added to the solution. The mixture was stirred at 0° C. for 30 minutes, then the solvent was evaporated under reduced pressure, and water was added to the residue. This mixture was extracted with dichloromethane, and the organic layer was washed with brine. The organic layer was dried over sodium sulfate, the solvent was evaporated under reduced pressure, and then 1,3-dimethylbarbituric acid (543 mg, 3.48 mmol) and tetrakis(tritriphenylphosphine)palladium (121 mg, 0.104 mmol) were added to the residue. The inside of the reaction vessel was degassed, and then substituted with argon, and the mixture was stirred at 35° C. for 21 hours. The reaction solution was suspended in saturated aqueous sodium carbonate, this suspension was extracted with dichloromethane, and the organic layer was washed with saturated aqueous sodium carbonate and brine. The organic layer was dried over sodium sulfate, the solvent was evaporated under reduced pressure, and then the residue was purified by column chromatography (silica gel, 50% ethyl acetate/n-hexane) to obtain 9-o-toluoyl-9H—Si-xanthene-3,6-diamine (135 mg, 0.39 mmol, yield 60%).

$^1$H-NMR (300 MHz, CDCl$_3$): δ 0.39 (s, 3H), 0.54 (s, 3H), 2.22 (s, 3H), 3.56 (s, 4H), 5.53 (s, 1H), 6.55 (dd, J=2.9 Hz, 8.0 Hz, 2H), 6.80 (d, J=8.0 Hz, 2H), 6.91 (d, J=2.9 Hz, 2H), 7.05-7.12 (m, 4H)

$^{13}$C-NMR (75 MHz, CDCl$_3$): δ −1.03, −0.42, 20.51 20.92, 50.07, 117.00, 118.96, 125.88, 126.11, 130.10, 131.11, 131.13, 134.15, 135.47, 139.11, 143.40, 145.89

HRMS (ESI+): Calcd for [M+H]+345.1787. Found 345.1739 (−4.8 mmu)

(3) 2-Me SiR600

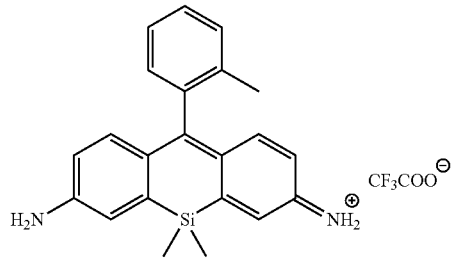

[Formula 22]

9-o-Toluyl-9H—Si-xanthene-3,6-diamine (35 mg, 0.102 mmol) was dissolved in dichloromethane (10 ml), p-chloranil (25 mg, 0.102 mmol) was added to the solution, and the mixture was stirred at room temperature for 2 hours. Water was added to the reaction solution, and the mixture was extracted with ethyl acetate. The organic layer was washed with brine, and dried over sodium sulfate, and then the solvent was evaporated under reduced pressure. The residue was purified by HPLC to obtain 2-Me SiR600 (26 mg, 0.057 mmol, yield 56%).

$^1$H-NMR (400 MHz, CD$_3$OD): δ 0.53 (s, 3H), 0.54 (s, 3H), 2.04 (s, 3H), 6.56 (dd, J=2.4 Hz, 9.2 Hz, 2H), 7.02 (d, J=9.2 Hz, 2H), 7.11 (s, 1H), 7.18 (d, J=2.4 Hz, 2H), 7.33-7.50 (m, 3H)

$^{13}$C-NMR (100 MHz, CD$_3$OD): δ −1.76, −1.51, 19.44, 116.87, 124.39, 126.74, 128.50, 130.05, 131.30, 136.86, 140.07, 143.85, 150.45, 158.52, 171.96

HRMS (ESI+): Calcd for [M]+343.1630. Found 343.1628 (−0.3 mmu)

(4) N-Acetyl-2-Me SiR600

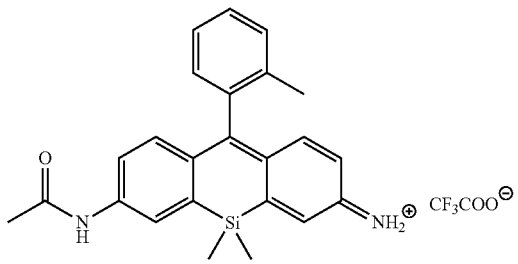

[Formula 23]

2-Me SiR600 (2.2 mg, 4.8 μmol) was dissolved in dimethylformamide (DMF, 4 ml), acetic anhydride (4.1 μl, 44.8 μmol) and pyridine (120 μl, 1.5 mmol) were added to the solution, and the mixture was stirred at room temperature for 40 hours. The reaction mixture was purified by HPLC to obtain N-acetyl-2-Me SiR600.

LRMS (ESI+) [M]+385

(5) N,N,N',N'-Tetraallyl-2-COOH SiR600

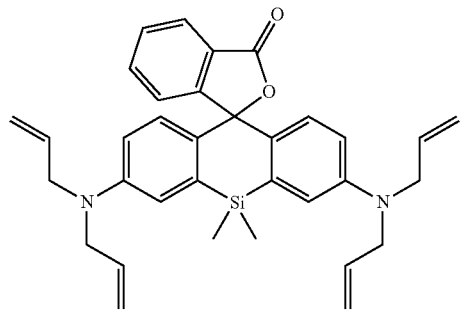

[Formula 24]

t-Butyl 2-bromobenzoate (3.6 g, 14.0 mmol) and anhydrous THF (40 mL) were added to a sufficiently dried flask under an argon atmosphere. The mixture was cooled to −78° C., and then 1 M sec-butyllithium (14 ml, 14.0 mmol) was added with, and the mixture was stirred for 3 minutes. N,N,N',N'-Tetraallyl-Si-xanthone (1.2 g, 2.8 mmol) dissolved in anhydrous THF (10 mL) was slowly added to the mixture at the same temperature, and the mixture was brought to room temperature. The mixture was stirred at room temperature for 20 minutes, and then 2 N hydrochloric acid (10 mL) was added, and the mixture was stirred for 10 minutes. The reaction mixture was extracted with dichloromethane, and the organic layer was washed with brine, and dried over sodium sulfate, and the solvent was evaporated under reduced pressure. Then, Trifluoroacetic acid (12 ml) was added to the residue, and the mixture was stirred at room temperature for 1 hour. The solvent was evaporated under reduced pressure, then water was added to the residue, and the mixture was extracted with dichloromethane. The organic layer was washed with brine, and dried over sodium sulfate, the solvent was evaporated under reduced pressure, and then the residue was purified by column chromatography (silica gel, 30% ethyl acetate/n-hexane) to obtain N,N,N',N'-tetraallyl-2-COOH SiR600 (935 mg, 1.75 mmol, yield 63%).

$^1$H-NMR (300 MHz, CDCl$_3$): δ 0.60 (s, 6H), 3.97 (d, J=5.1 Hz, 8H), 5.17-5.23 (m, 8H), 5.75-5.88 (m, 4H), 6.68 (dd, J=3.0 Hz, 6.8 Hz, 2H), 6.83 (d, J=6.8 Hz, 2H), 7.15 (d, J=3.0 Hz, 2H), 7.37 (d, J=7.1 Hz, 1H), 7.59 (t, J=7.1 Hz, 1H), 7.70 (t, J=7.1 Hz, 1H), 7.99 (d, J=7.1 Hz, 1H)

$^{13}$C-NMR (100 MHz, CDCl$_3$): δ −2.03, 0.40, 52.76, 92.12, 112.97, 116.22, 116.82, 124.98, 125.63, 127.58, 128.13, 128.69, 131.90, 133.39, 133.66, 137.32, 147.51, 153.68, 170.44

HRMS (ESI+): Calcd for [M+H]+ 533.2624. Found 533.2593 (−3.1 mmu)

(6) 2-COOH SiR600

[Formula 25]

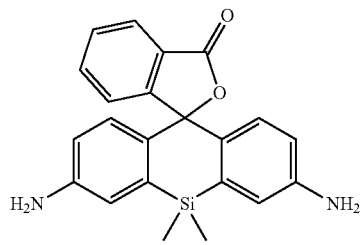

N,N,N',N'-tetraallyl-2-COOH SiR600 (310 mg, 0.58 mmol) was dissolved in dichloromethane (30 ml), and 1,3-dimethylbarbituric acid (454 mg, 2.91 mmol) and tetrakis(tritriphenylphosphine)palladium (101 mg, 0.087 mmol) were added to the solution. The inside of the reaction vessel was degassed, and then substituted with argon, and the mixture was stirred at 35° C. for 20 hours. The reaction solution was suspended in saturated aqueous sodium carbonate, and the mixture was extracted with dichloromethane. The organic layer was washed with saturated aqueous sodium carbonate and brine, and dried over sodium sulfate, the solvent was evaporated under reduced pressure, and then the residue was purified by column chromatography (silica gel, 80% ethyl acetate/n-hexane) to obtain 2-COOH SiR600 (114 mg, 0.31 mmol, yield 53%).

$^1$H-NMR (400 MHz, DMF-d$_7$): δ 0.65 (s, 3H), 0.73 (s, 3H), 6.74-6.75 (m, 4H), 7.23 (s, 2H), 7.56 (d, J=7.7 Hz, 1H), 7.85 (t, J=7.7 Hz, 1H), 7.99 (t, J=7.7 Hz, 1H), 8.12 (d, J=7.2 Hz, 1H)

$^{13}$C-NMR (400 MHz, DMF-d$_7$): δ −1.62, 0.33, 92.50, 115.72, 119.33, 125.46, 125.78, 127.16, 128.44, 129.81, 132.42, 134.91, 137.14, 149.16, 155.28, 170.72

HRMS (ESI+): Calcd for [M+H]+ 373.1372. Found 373.1347 (−2.5 mmu)

(7) N-Acetyl-2-COOH SiR600

[Formula 26]

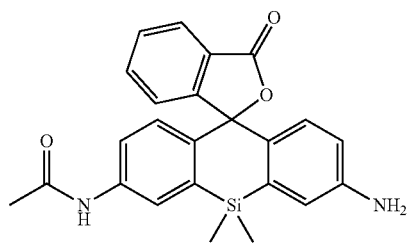

2-COOH SiR600 (8 mg, 21.4 mop was dissolved in DMF (6 ml), acetic anhydride (2.0 μl, 21.4 μmmol) and pyridine (400 μl, 5.06 mmol) were added to the solution, and the mixture was stirred at room temperature for 24 hours. The solvent was evaporated under reduced pressure, water was added to the residue, and the mixture was extracted with dichloromethane. The organic layer was washed with brine, the solvent was evaporated, and the residue was purified by HPLC to obtain N-acetyl-2-COOH SiR600 (1.0 mg, 2.4 mmol, yield 11%).

HRMS (ESI+): Found 415.1453, calculated 415.1478 for [M+H]+ (−2.5 mmu)

Example 3

Figure 2:
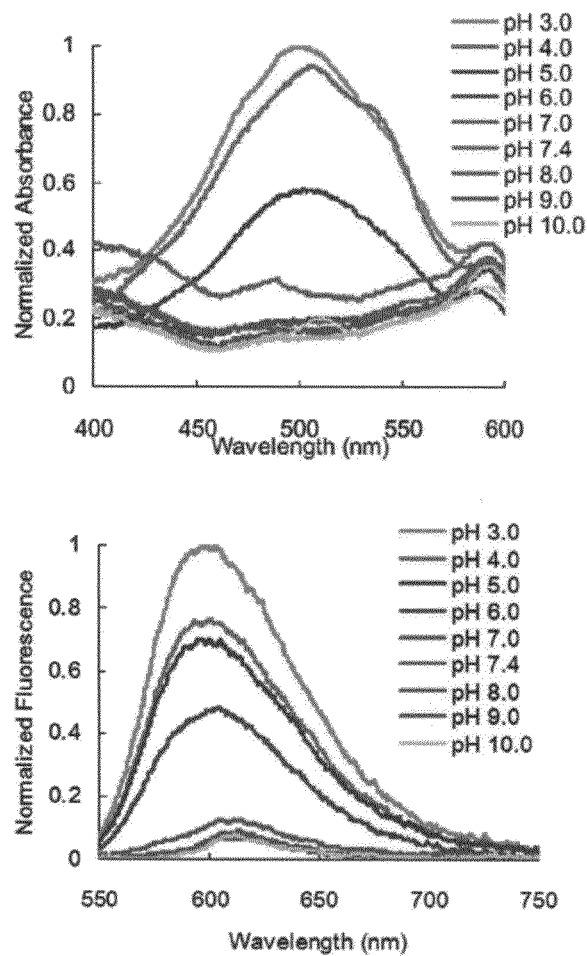
FIG. 2 shows pH profiles of absorption spectrum (upper graph) and fluorescence spectrum (lower graph) of N-acetyl-2-Me SiR600 (Example 2, (4)) observed in a 0.1 M sodium phosphate buffer containing 1% DMSO. Fluorescence was measured with an excitation wavelength of 505 nm.

Absorption and fluorescence spectra as well as pH profiles of 2-Me SiR600 and the acetylated compound thereof (N-Ac-2-Me SiR600) synthesized in Example 2 were measured. The results are shown in FIGS. 1 and 2, and Table 1. Because of the acetylation of the amino group at the 3-position of the xanthene ring, maximum absorption wavelength of N-Ac-2-Me SiR600 significantly shifted to the shorter wavelength side compared with 2-Me SiR600. Further, although absorbance of the acetylated compound decreased with decrease of pH, 2-Me SiR600 did not substantially show pH-dependent change of absorbance. Therefore, 2-Me SiR600 in which the amino group at the 3-position is acylated can be functioned as a fluorescent probe for detecting enzymatic activity on the basis of absorption wavelength change with a high S/N ratio, without using the intramolecular photoinduced electron transfer.

TABLE 1

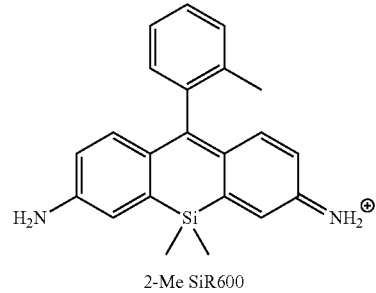 [SMILES: Cc1ccccc1C1=C2C=CC(=[NH2+])C=C2[Si](C)(C)c2cc(N)ccc21]

2-Me SiR600

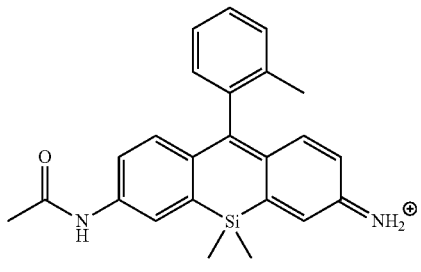

N-Ac-2-Me SiR600

| | $\lambda_{abs}$ (nm) | $\lambda_{fl}$ (nm) |
|---|---|---|
| 2-Me SiR600 | 593 | 613 |
| N-Ac-2-Me SiR600 | 505 | 600 |

Figure 3:
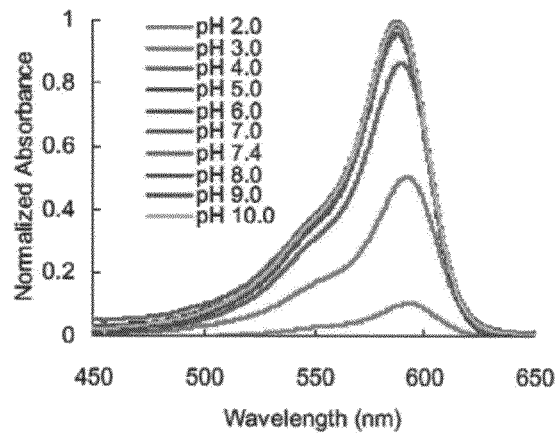
FIG. 3 shows pH profiles of absorption spectrum (upper graph) and fluorescence spectrum (lower graph) of 2-COOH SiR600 (Example 2, (6)) observed in a 0.1 M sodium phosphate buffer containing 1% DMSO. Fluorescence was measured with an excitation wavelength of 590 nm.
Figure 3:
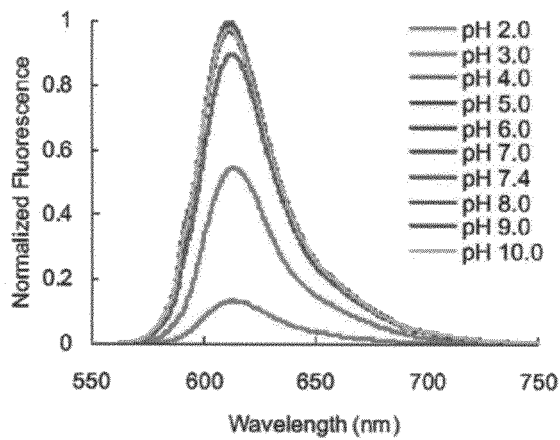
Figure 4:
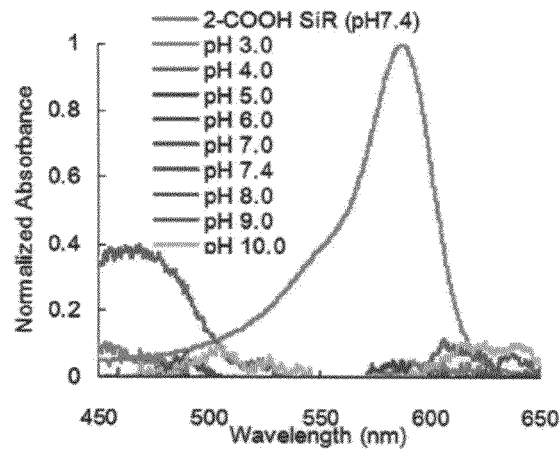
FIG. 4 shows pH profiles of absorption spectra of 2-COOH SiR600 (Example 2, (6), 1 µM) and N-acetyl-2-COOH SiR600 (Example 2, (7), 1 µM) observed in a 0.1 M sodium phosphate buffer containing 1% DMSO.

In a similar manner, absorption and fluorescence spectra as well as pH profiles of 2-COOH SiR600 and the acetylated compound thereof were measured. The results are shown in FIGS. 3 and 4, and Table 2. As shown in FIG. 4, 2-COOH SiR600 was made by the acetylation not to show absorption for the visible region in the physiological pH range, and 2-COOH SiR600 did not substantially show absorbance change at pH higher than the physiological pH region. Therefore, it can be used as a fluorescent probe as shown in the following scheme.

TABLE 2

[Formula 27]

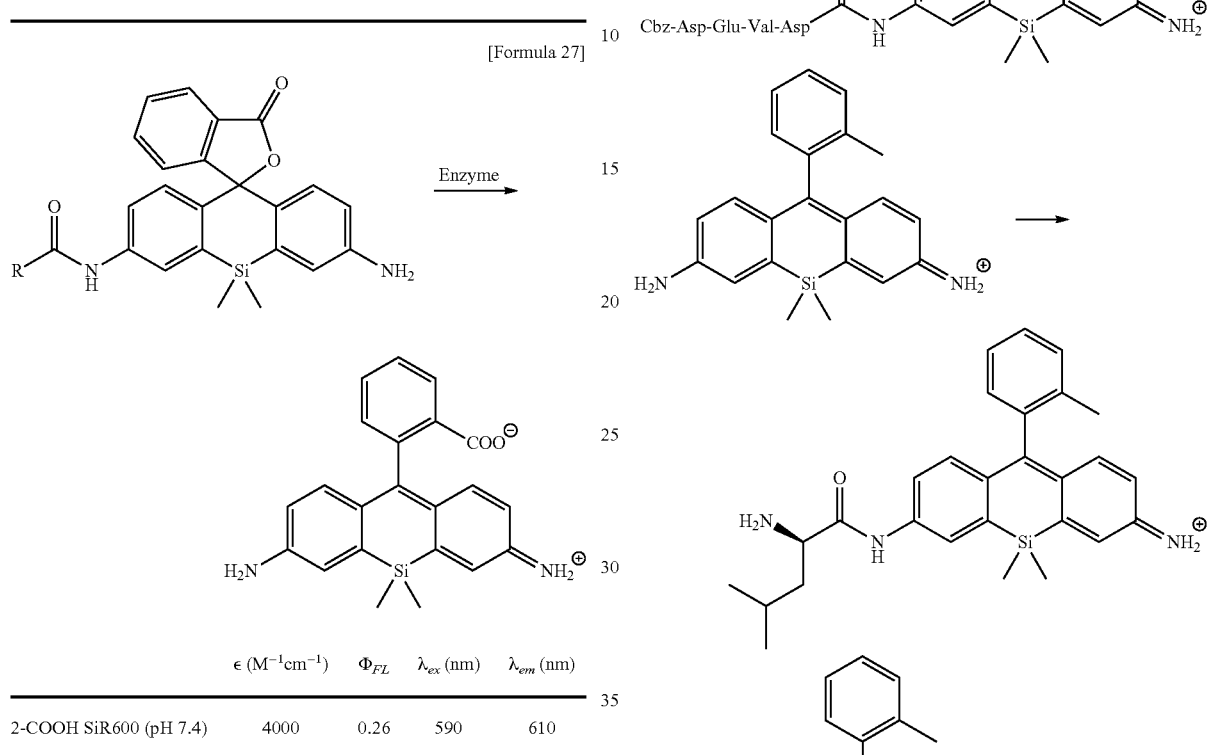

| | ε (M⁻¹cm⁻¹) | $\Phi_{FL}$ | $\lambda_{ex}$ (nm) | $\lambda_{em}$ (nm) |
|---|---|---|---|---|
| 2-COOH SiR600 (pH 7.4) | 4000 | 0.26 | 590 | 610 |

Example 4

By using 2-Me SiR600 synthesized in Example 2 as a starting compound, a fluorescent probe for measuring caspase-3 activity in which an oligopeptide residue (Cbz-Asp-Glu-Val-Asp) was introduced as $R^{10}$ (Z-DEVD-SiR600, Cbz and Z mean benzyloxycarbonyl group), and a probe for detecting leucine aminopeptidase (LAP) activity in which a leucine residue (Leu) was introduced as $R^{10}$ (Leu-SiR600) were synthesized by the steps shown in the following scheme.

[Formula 28]

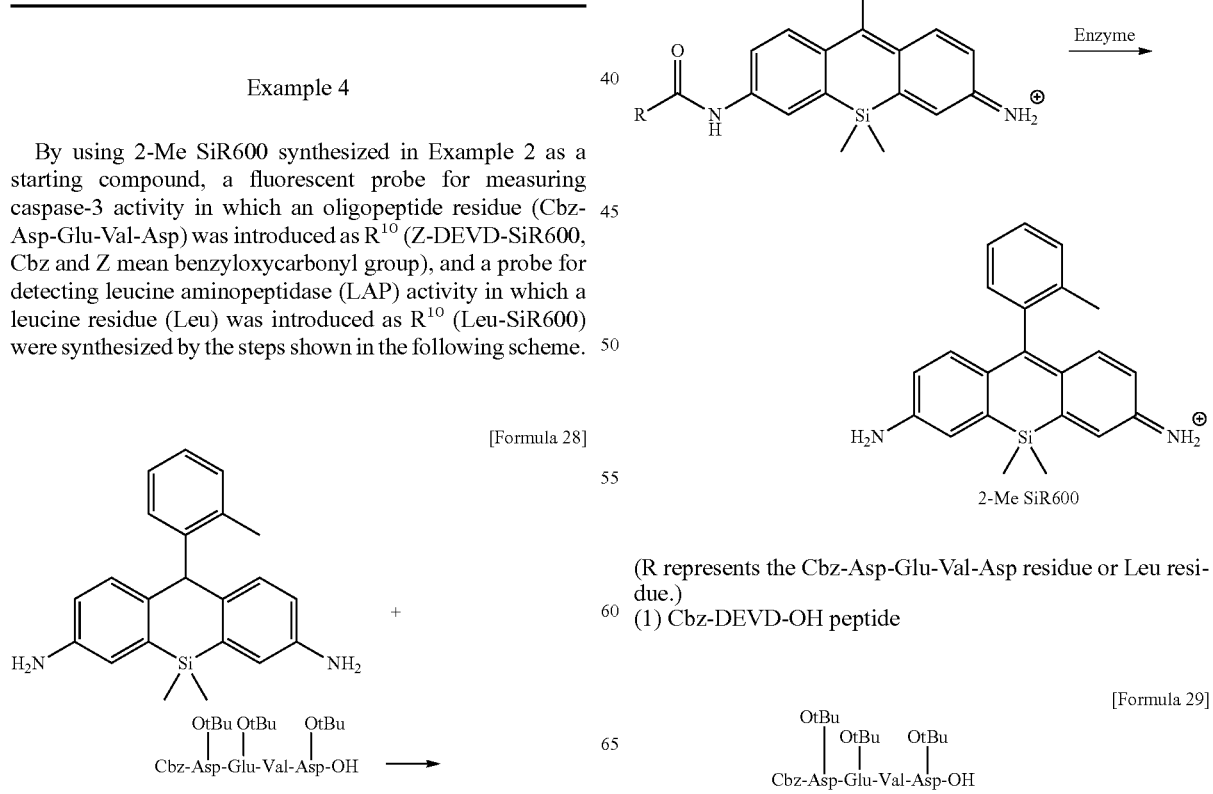

(R represents the Cbz-Asp-Glu-Val-Asp residue or Leu residue.)

(1) Cbz-DEVD-OH peptide

[Formula 29]

The Cbz-DEVD-OH peptide was synthesized by using 2-chlorotrityl chloride resin (1.3 mmol/g, 100 to 200 mesh, 1% DVB) according to the usual Fmoc solid phase synthesis method.

(a) Peptide Coupling Cycle

Fmoc amino acids (5 equivalents of the resin), and O-(7-azabenzotriazol-1-yl)-N,N,N,N-tetramethyluronium hexafluorophosphate (HATU, 5 equivalents of the resin) were dissolved in DMF, diisopropylethylamine (DIPEA, 10 equivalents of the resin) was added to the solution, and the mixture was stirred. This solution was added to a resin coupled with the peptide of which N-terminus was deprotected, and the mixture was stirred for 40 minutes.

(b) Fmoc Deprotection Cycle

Removal of the Fmoc protective group was performed by adding a 20% (v/v) piperidine solution in DMF to the resin, and stirring the mixture for 12 minutes.

(c) Cleavage from Resin

A solution of trifluoroacetic acid and dichloromethane (2:98) was added to the resin, and stirring of the mixture for 1 minute was repeated 10 times to cleave the Cbz-DEVD-OH peptide from the resin. The resin was removed by filtration, and the filtrate was evaporated under reduced pressure. Excess amount of cold water was added to the residue, and the resulting precipitates were collected by filtration to obtain the Cbz-DEVD-OH peptide.

HRMS (ESI+): Calcd for [M+Na]+ 801.3898. Found 801.3904 (+0.6 mmu)

(2) Z-DEVD-SiR600

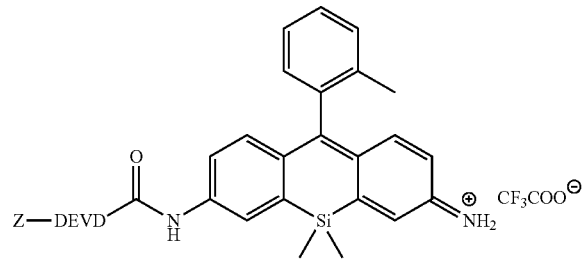

[Formula 30]

9-o-Toluyl-9H—Si-xanthene-3,6-diamine (48 mg, 0.14 mmol) was dissolved in DMF (10 ml), Cbz-DEVD-OH (120 mg, 0.154 mmol), HATU (117 mg, 0.308 mmol), 1-hydroxy-1H-benzotriazole monohydrate (HOBt•H$_2$O, 47 mg, 0.308 mmol), and DIPEA (79 µl, 0.616 mmol) were added to the solution, and the mixture was stirred at room temperature for 39 hours. Water was added to the reaction mixture, the mixture was extracted with dichloromethane, and the organic layer was washed with brine, and dried over sodium sulfate. Then, the solvent was evaporated under reduced pressure. The residue was dissolved in dichloromethane (20 ml), p-chloranil (34.4 mg, 0.14 mmol) was added to the solution, and the mixture was stirred at room temperature for 3 hours. Water was added to the reaction mixture, and the mixture was extracted with dichloromethane. The organic layer was washed with saturated aqueous sodium hydrogencarbonate and brine, and dried over sodium sulfate, and then the solvent was evaporated under reduced pressure. Trifluoroacetic acid (10 ml) was added to the residue, the mixture was stirred at room temperature for 1 hour, and then the solvent was evaporated under reduced pressure. The residue was purified by HPLC (eluent, 40% acetonitrile/0.1% trifluoroacetic acid/water (0 minute) to 52% acetonitrile/0.1% TFA/water (15 minutes); flow rate, 5.0 mL/min) to obtain Z-DEVD-SiR600 (6.5 mg, 6.2 yield 4%).

HRMS (ESI+): Calcd for [M]+ 935.3647. Found 935.3617 (−3.1 mmu)

In the HPLC chromatogram of the purified compound (linear gradient of from 16% acetonitrile/0.1% trifluoroacetic acid/water to 80% acetonitrile/0.1% trifluoroacetic acid/water; flow rate, 1.0 mL/min; Abs., 500 nm), a single peak was observed at 15.8 minutes.

Figure 5:
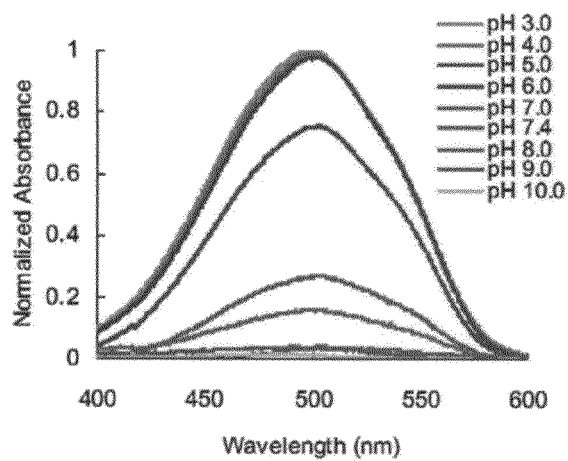
FIG. 5 shows pH profile of absorption spectrum of Z-DEVD-SiR600 (Example 4, (2)) observed in a 0.1 M sodium phosphate buffer containing 1% DMSO. The lower chemical formula shows a scheme as explanation of pH-dependent decrease of absorption of Z-DEVD-SiR600.
Figure 5:
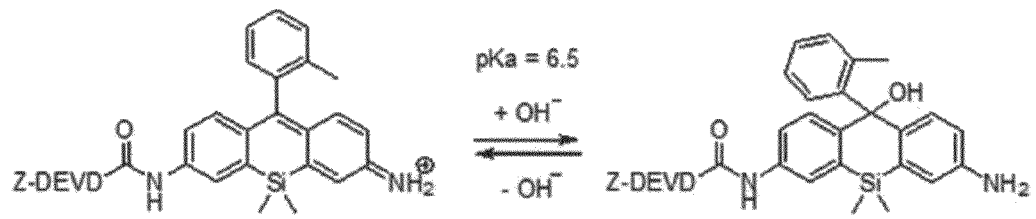

Absorption spectrum of Z-DEVD-SiR600 was measured in a 0.1 M sodium phosphate buffer of pH 3 to 10 containing 1% DMSO. The measurement results are shown in FIG. 5, and the photochemical characteristics are shown in Table 3 mentioned below together with the results for SiR600.

Although Z-DEVD-SiR600 showed pH-dependent absorbance change, it did not absorb light around the maximum absorption wavelength (593 nm) of SiR600, which is produced by contact with caspase-3, and thus it was confirmed that the caspase-3 activity measurement utilizing excitation light of around 593 nm could be performed without influence of Z-DEVD-SiR600.

TABLE 3

| | $\epsilon$ (M$^{-1}$cm$^{-1}$) | $\Phi_{FL}$ | $\lambda_{ex}$ (nm) | $\lambda_{em}$ (nm) |
|---|---|---|---|---|
| 2-Me SiR600 (pH 7.4) | 91000 | 0.38 | 593 | 613 |
| Z-DEVD-SiR600 (pH 3.0) | 85000 | 0.19 | 500 | 600 |

(3) Leu-SiR600

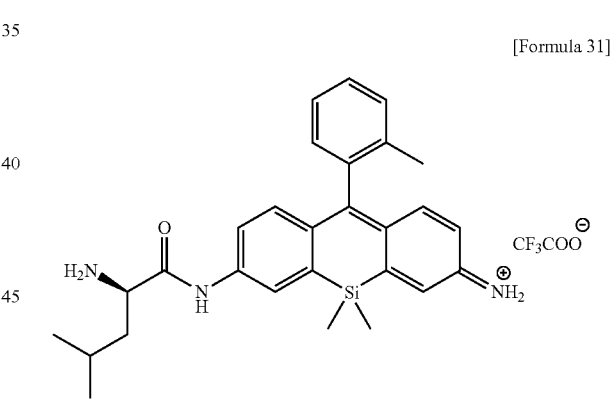

[Formula 31]

2-Me SiR600 (3 mg, 6.5 µmmol) was dissolved in DMF (6 ml), Boc-Leu-OH—H$_2$O (17.1 mg, 68.7 µmol), HATU (22 mg, 57.9 µmol), HOBt•H$_2$O (6.8 mg, 44.4 µmol), and DIPEA (14.2 µl, 111 µmmol) were added to the solution, and the mixture was stirred at room temperature for 25 hours. The solvent was evaporated under reduced pressure, then water was added to the residue, and the mixture was extracted with dichloromethane. The organic layer was washed with brine, and dried over sodium sulfate, and the solvent was evaporated under reduced pressure. Trifluoroacetic acid (6 ml) was added to the residue, the mixture was stirred at room temperature for 1 hour, and then the solvent was evaporated under reduced pressure. The residue was purified by HPLC (eluent, 32% acetonitrile/0.1% trifluoroacetic acid/water (0 minute) to 48% acetonitrile/0.1% trifluoroacetic acid/water (20 minutes); flow rate, 5.0 mL/min) to obtain Leu-SiR600 (1.4 mg, 2.46 µmol, 38%).

HRMS (ESI+); Calcd for [M]+456.2471. Found 456.2425 (−4.7 mmu)

In the HPLC chromatogram of the purified compound (linear gradient of from 16% acetonitrile/0.1% trifluoroacetic acid/water to 80% acetonitrile/0.1% trifluoroacetic acid/water; flow rate, 1.0 mL/min; Abs., 500 nm), a single peak was observed at 13.5 minutes.

Example 5

Figure 6:
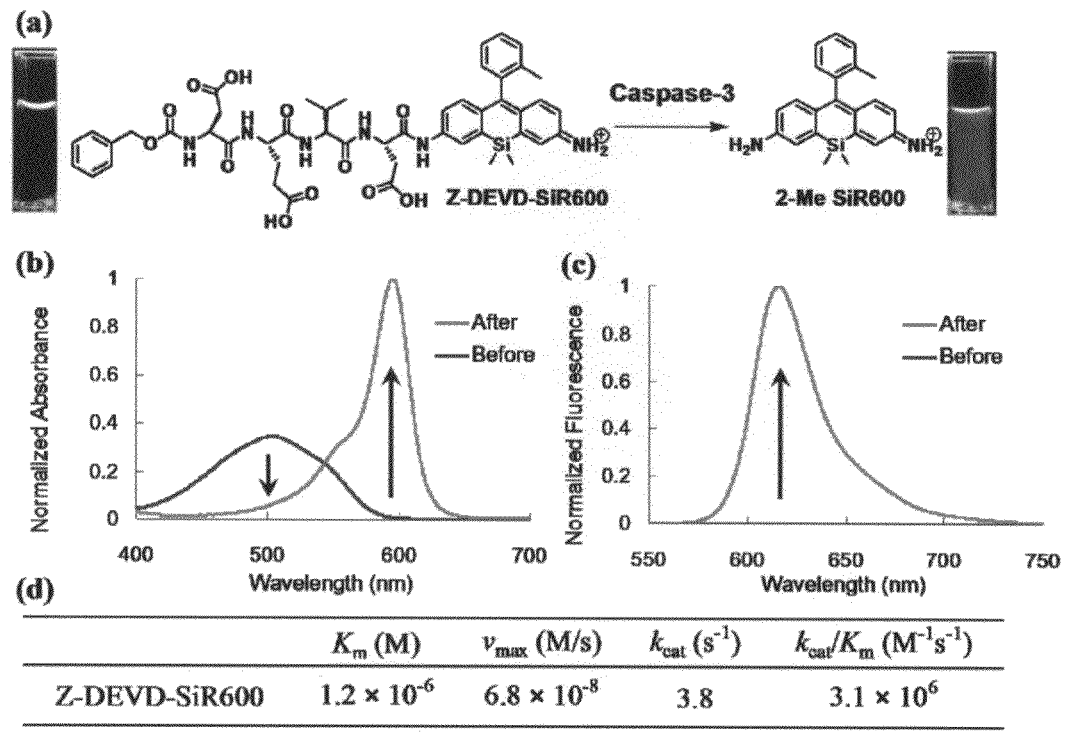
FIG. 6 shows the reaction scheme of the reaction of Z-DEVD-SiR600 (Example 4, (2)) and caspase-3 (a), change of absorption spectrum induced by the reaction (b), change of fluorescence spectrum induced by the reaction (c), and kinetic parameters of the reaction (d). Fluorescence was measured with an excitation wavelength of 593 nm.

Function of Z-DEVD-SiR600 as a fluorescent probe was evaluated by reacting it with caspase-3. Caspase-3 (0.5 µg) was added to Z-DEVD-SiR600 (2 µM), and the mixture was reacted for 10 hours. The reaction was performed at 37° C. in a 20 mM HEPES buffer (pH 7.4, 0.75 ml) containing 100 µM dithiothreitol (DTT), 10% glycerol, 0.1% CHAPS, 100 mM NaCl, and 0.1% DMSO. The absorption spectra and fluorescence spectra observed before and after the reaction (excitation wavelengths are shown in FIG. 6, (b) and (c), respectively, and the kinetics parameters of the reaction are shown in FIG. 6, (d)). As shown in FIG. 6, (b), Z-DEVD-SiR600 has the absorption maximum wavelength of around 500 nm, whereas 2-Me SiR600 produced by the reaction of Z-DEVD-SiR600 and the caspase-3 shows the absorption maximum at 593 nm. Therefore, if the measurement is performed before and after the reaction with an excitation light of 593 nm, fluorescence is scarcely observed before the reaction, but extremely strong fluorescence is observed after the reaction as shown in FIG. 6, (c). That is, it was demonstrated that Z-DEVD-SiR600 could be preferably used as a fluorescent probe for caspase-3.

Example 6

Figure 7:
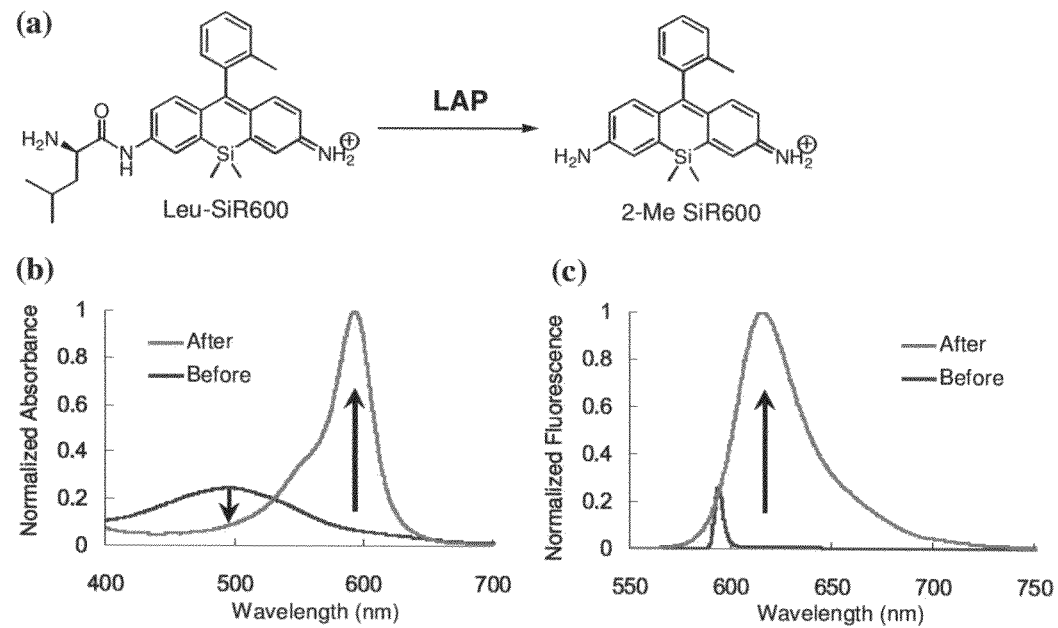
FIG. 7 shows a reaction scheme of the reaction of Leu-SiR600 (Example 4, (3)) and LAP (a), change of absorption spectrum induced by the reaction (b), and change of fluorescence spectrum induced by the reaction (c). Fluorescence was measured with an excitation wavelength of 593 nm.

Function of Leu-SiR600 as a fluorescent probe was evaluated by reacting it with leucine aminopeptidase. Leucine aminopeptidase (0.096 unit) was added to Leu-SiR600 (6 µM), and the mixture was reacted for 2.5 hours. The reaction performed at 37° C. in a 0.1 M sodium phosphate buffer (pH 7.4, 0.75 ml) containing 0.8% DMSO. The absorption spectra and fluorescence spectra observed before and after the reaction are shown in FIG. 7, (b) and (c), respectively. As shown in FIG. 7, (b), Leu-SiR600 shows the absorption maximum wavelength around 500 nm, whereas 2-Me SiR600, which is generated by the reaction of Leu-SiR600 with leucine aminopeptidase, shows the maximum absorption at 593 nm. Therefore, if the measurement is performed before and after the reaction with an excitation light of 593 nm, fluorescence is scarcely observed before the reaction, but extremely strong fluorescence is observed after the reaction as shown in FIG. 7, (c). That is, it was demonstrated that Leu-SiR600 could be preferably used as a fluorescent probe for leucine aminopeptidase.

On the basis of the results of caspase-3 measurement using Z-DEVD-SiR600 and the results of leucine aminopeptidase measurement using Leu-SiR600 obtained in Examples 5 and 6, it was demonstrated that the compounds represented by the general formula (I) (in the formula, $R^9$ and/or $R^{10}$ represents a monovalent substituent that is cleaved by contact with an object substance for measurement) and salts thereof provided by the present invention can be preferably used as a fluorescent probe for peptidase or protease measurement.

INDUSTRIAL APPLICABILITY

The compounds represented by the general formula (I) and salts thereof provided by the present invention have a property that the fluorescence characteristics thereof change after trapping an object substance for measurement, and can be utilized as compounds for manufacture of a fluorescent probe that enables high sensitivity measurement of an object substance for measurement such as metal ions, reactive oxygen species, proton, and enzymatic activities.

What is claimed is:
1. A compound of formula (I) or a salt thereof:

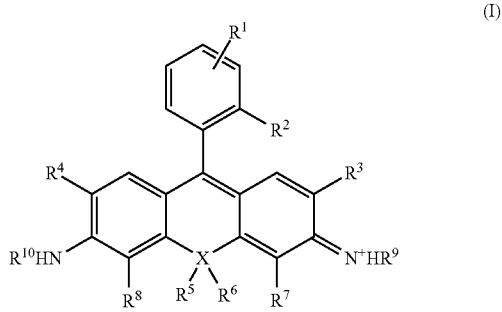

wherein, $R^1$ represents the same or different 1 to 4 monovalent substituents; $R^2$ represents a monovalent substituent; $R^3$ and $R^4$ independently represent a hydrogen atom, or an alkyl group having 1 to 6 carbon atoms; $R^5$ and $R^6$ independently represent an alkyl group having 1 to 6 carbon atoms, or an aryl group; $R^7$ and $R^8$ independently represent a hydrogen atom, or an alkyl group having 1 to 6 carbon atoms; $R^9$ and $R^{10}$ independently represent a hydrogen atom, or a monovalent substituent; and X represents a silicon atom, a germanium atom, or a tin atom.

2. The compound or a salt thereof according to claim 1, wherein X is a silicon atom or a germanium atom.

3. The compound or a salt thereof according to claim 1, wherein $R^1$ or $R^2$ is a trapping group that can trap a proton, a metal ion, a reactive oxygen species, a hypoxic environment, an enzyme activity, or glutathione, and $R^9$ and $R^1$ are hydrogen atoms.

4. The compound or a salt thereof according to claim 1, wherein at least one of $R^9$ and $R^{10}$ is a trapping group that can trap a proton, a metal ion, a reactive oxygen species, a hypoxic environment, an enzyme activity, or glutathione, and $R^1$ and $R^2$ are hydrogen atoms.

5. The compound or a salt thereof according to claim 4, wherein at least one of $R^9$ and $R^{10}$ is a trapping group that can trap an activity of an enzyme selected from the group consisting of a peptidase, a protease, a lactamase, a glycoside hydrolase, a transferase, and an oxidoreductase.

6. The compound or a salt thereof according to claim 4, wherein at least one of $R^9$ and $R^{10}$ is a trapping group that is cleaved by an enzyme selected from the group consisting of a peptidase, a protease, and a lactamase.

7. The compound or a salt thereof according to claim 4, wherein at least one of $R^9$ and $R^{10}$ is a trapping group that is cleaved by a peptidase or a protease selected from the group consisting of caspase, prostate-specific antigen, leucine aminopeptidase, and γ-glutamyl transpeptidase.

8. A fluorescent probe comprising the compound or salt thereof according to claim 1.

9. The compound or a salt thereof according to claim 1, wherein $R^1$ or $R^2$ is a trapping group that can trap a proton, a metal ion, a reactive oxygen species, a hypoxic environment, an enzyme activity, or glutathione, provided that $R^1$ and $R^2$ are not simultaneously trapping groups, and at least one of $R^9$ and $R^{10}$ is a trapping group that can trap a proton, a metal ion, a reactive oxygen species, a hypoxic environment, an enzyme activity, or glutathione.

10. A method for measuring an object substance for measurement, comprising:
   (a) contacting the compound or a salt thereof according to claim 1 with the object substance for measurement, and
   (b) measuring fluorescence intensity of a compound generated in (a) after trapping of the object substance for measurement.

11. A method for preparing the compound or a salt thereof according to claim 1 wherein $R^3$ and $R^4$ represent a hydrogen atom, $R^5$ and $R^6$ independently represent an alkyl group having 1 to 6 carbon atoms, or an aryl group; $R^7$ and $R^8$ represent hydrogen atom; $R^9$ and $R^{10}$ represent hydrogen atom; and X represents a silicon atom, a germanium atom, or a tin atom, comprising:
   (a) preparing a compound of formula (II):

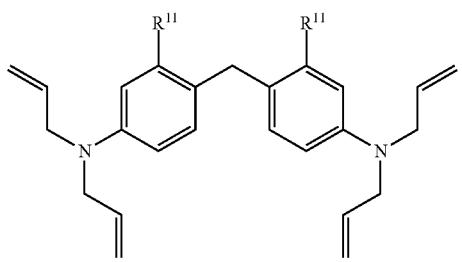

(II)

wherein $R^{11}$ represents a halogen atom, from a 3-halogenated N,N-diallylaniline prepared from a 3-halogenated aniline and an allyl halide, and formaldehyde,
   (b) reacting the compound of formula (II) with a dichlorodialkylsilane, and then subjecting the resultant to an oxidation reaction to prepare an N,N,N',N'-tetrallyl-diamino-Si-xanthone mentioned as shown below,

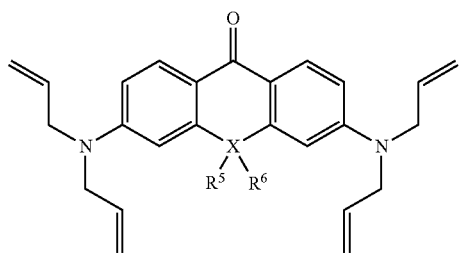

(c) preparing a compound of formula (III):

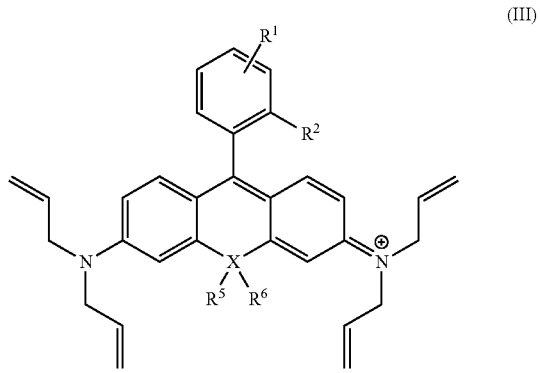

(III)

wherein, $R^1$ represents the same or different 1 to 4 monovalent substituents and $R^2$ represents a monovalent substituent wherein $R^1$ and $R^2$ optionally include protective groups for the preparation of the compound of formula (III), from N,N,N',N'-tetrallyl-diamino-X-xanthone and a halogenated benzene derivative,
   (d) deallylating the compound of formula (III) to prepare the compound according to claim 1, wherein when $R^1$ and $R^2$ include protective groups for the preparation of the compound of the general formula (III), removal of the protective group may be performed before or after, or simultaneously with the deallylation.

12. A compound of formula (III) or a salt thereof:

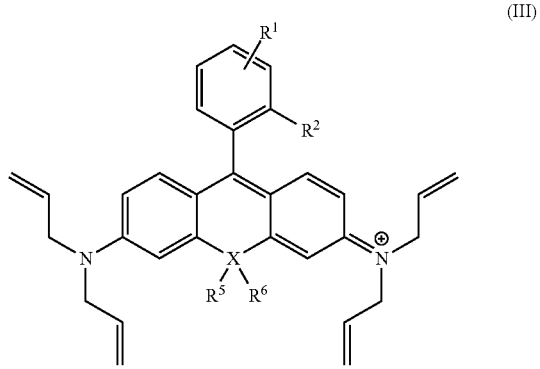

(III)

wherein, $R^1$ represents the same or different 1 to 4 monovalent substituents and $R^2$ represents a monovalent substituent; $R^5$ and $R^6$ independently represent an alkyl group having 1 to 6 carbon atoms, or an aryl group; and X represents a silicon atom, a germanium atom, or a tin atom.

* * * * *